(12) United States Patent
Namiki et al.

(10) Patent No.: US 9,383,704 B2
(45) Date of Patent: Jul. 5, 2016

(54) GRAMMAGE DETECTION SENSOR FOR RECORDING MATERIAL AND IMAGE FORMING APPARATUS

(71) Applicant: CANON KABUSHIKI KAISHA, Tokyo (JP)

(72) Inventors: Teruhiko Namiki, Mishima (JP); Shuhei Watanabe, Yokohama (JP); Yasutaka Yagi, Mishima (JP); Tsutomu Ishida, Suntou-gun (JP); Tadashi Okanishi, Mishima (JP); Motoyasu Muramatsu, Susono (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 14/572,632

(22) Filed: Dec. 16, 2014

(65) Prior Publication Data

US 2015/0177663 A1 Jun. 25, 2015

(30) Foreign Application Priority Data

Dec. 19, 2013 (JP) .................................. 2013-262773
Nov. 26, 2014 (JP) ................................. 2014-238974

(51) Int. Cl.
*G03G 15/00* (2006.01)
*G01B 17/02* (2006.01)
(Continued)

(52) U.S. Cl.
CPC ............ *G03G 15/5029* (2013.01); *G01B 17/02* (2013.01); *G01N 29/11* (2013.01); *G01N 29/27* (2013.01); *G03G 15/6594* (2013.01); *G01N 2223/642* (2013.01); *G01N 2291/0237* (2013.01); *G01N 2291/02818* (2013.01);

(Continued)

(58) Field of Classification Search
CPC .......... G03G 15/5029; G03G 15/6594; G03G 2215/00637; G03G 2215/00738; G03G 2215/00742; G01N 29/11; G01N 29/27; G01N 29/30; G01N 29/32; G01N 29/323; G01N 29/326; G01N 2223/642; G01N 2291/0237; G01B 17/02
USPC ............ 399/45, 389; 702/103, 171, 173, 175; 73/580, 599, 646, 602, 159
See application file for complete search history.

(56) References Cited

U.S. PATENT DOCUMENTS 4,446,735 A 5/1984 Weilacher
7,130,245 B2 * 10/2006 Okitsu et al. .................. 367/125
(Continued)

FOREIGN PATENT DOCUMENTS

JP 01-039540 B 8/1989
JP 2004107030 A * 4/2004
(Continued)

*Primary Examiner* — Robert Beatty
(74) *Attorney, Agent, or Firm* — Canon U.S.A., Inc. IP Division

(57) ABSTRACT

A grammage detection sensor according to an aspect of the present invention includes a transmission unit configured to transmit an ultrasonic wave, a reception unit configured to receive the ultrasonic wave transmitted from the transmission unit, and a control unit configured to detect a grammage of a recording material, when a plurality of recording materials are continuously conveyed between the transmission unit and the reception unit, on the basis of a first ultrasonic wave received by the reception unit after the ultrasonic wave is transmitted by the transmission unit between a preceding recording material and a recording material following the preceding recording material, and a second ultrasonic wave received via a recording material by the reception unit after the ultrasonic wave is transmitted by the transmission unit.

26 Claims, 11 Drawing Sheets

(51) Int. Cl.
  *G01N 29/27* (2006.01)
  *G01N 29/11* (2006.01)

(52) U.S. Cl.
  CPC .......... *G01N2291/102* (2013.01); *G03G 15/80* (2013.01); *G03G 2215/00637* (2013.01); *G03G 2215/00742* (2013.01); *G03G 2215/00751* (2013.01)

(56) References Cited

U.S. PATENT DOCUMENTS

| | | | |
|---|---|---|---|
| 8,045,868 B2 * | 10/2011 | Kuramochi et al. | 399/45 |
| 8,256,294 B2 * | 9/2012 | Ishida | 73/596 |
| 8,570,622 B2 * | 10/2013 | Pellaton et al. | 358/498 |
| 8,635,912 B2 * | 1/2014 | Aoki | 73/597 |
| 8,904,874 B2 * | 12/2014 | Knorr | 73/632 |
| 2009/0310992 A1 * | 12/2009 | Iwasa et al. | 399/45 |
| 2011/0142461 A1 * | 6/2011 | Nakamura et al. | 399/45 |
| 2013/0039672 A1 * | 2/2013 | Ishida | 399/45 |
| 2015/0160598 A1 * | 6/2015 | Yagi et al. | G03G 15/5029 |

FOREIGN PATENT DOCUMENTS

| | | | |
|---|---|---|---|
| JP | 2004219856 A | * | 8/2004 |
| JP | 2010-18433 A | | 1/2010 |
| JP | 2011037524 A | * | 2/2011 |
| JP | 2012-123125 A | | 6/2012 |
| JP | 2013-40016 A | | 2/2013 |
| JP | 2013-056771 A | | 3/2013 |

* cited by examiner

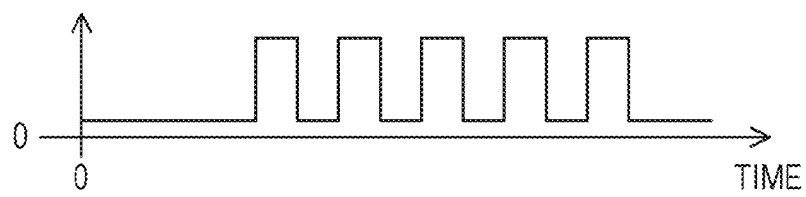
FIG. 3A
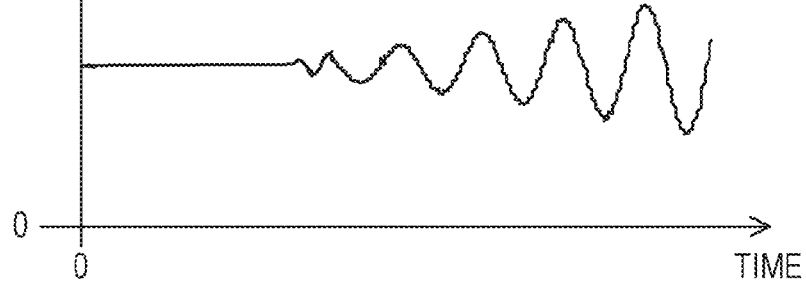
FIG. 3B
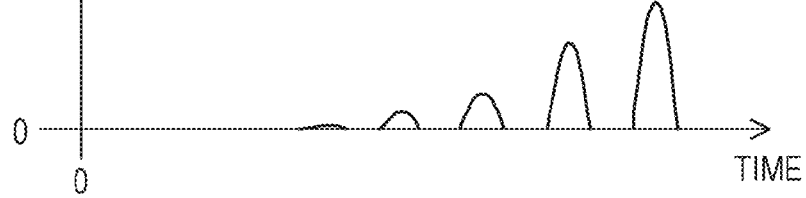
FIG. 3C
FIG. 4
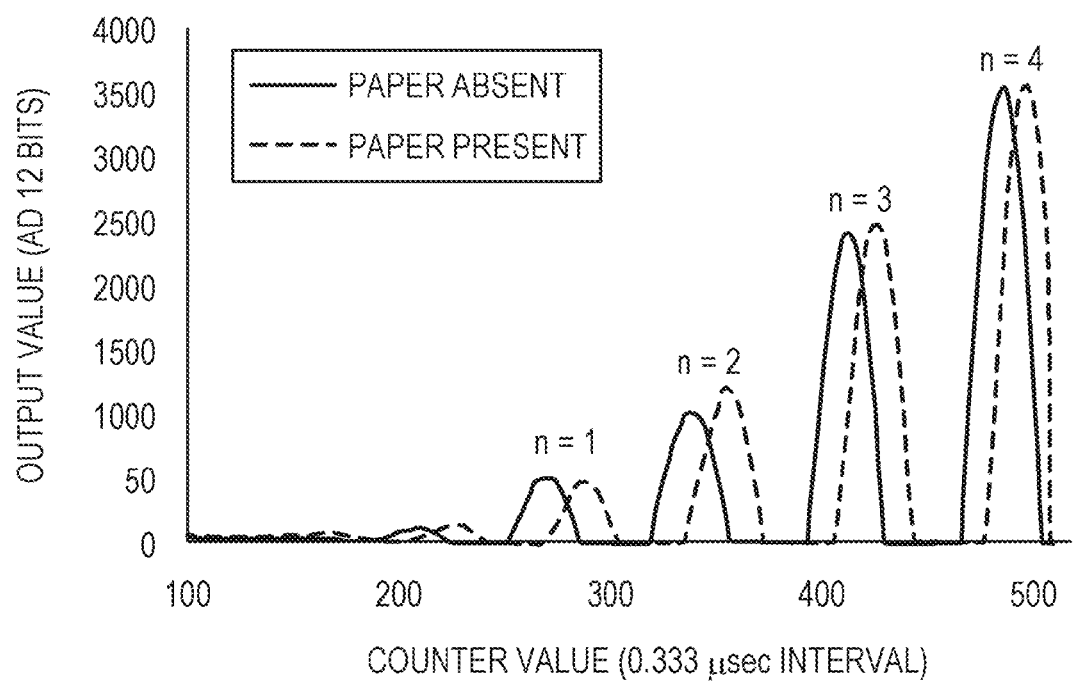

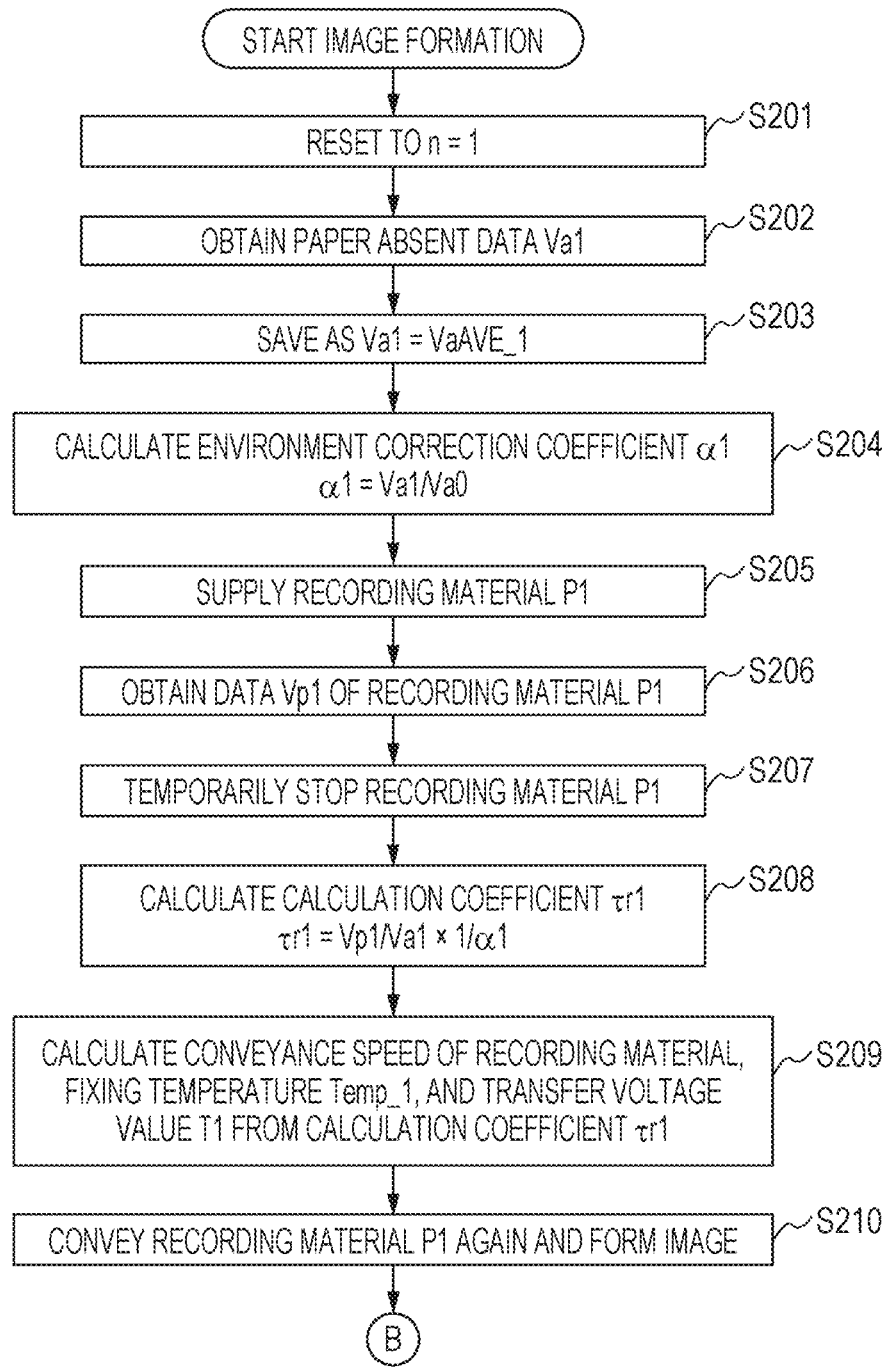

GRAMMAGE DETECTION SENSOR FOR RECORDING MATERIAL AND IMAGE FORMING APPARATUS

BACKGROUND OF THE INVENTION

1. Field of the Invention

The present invention relates to a technology for accurately detecting a grammage of a recording material.

2. Description of the Related Art

Up to now, some image forming apparatuses such as a copier and a printer are provided with a sensor configured to determine a type of a recording material inside thereof. In these apparatuses, the type of the recording material is automatically determined, and transfer conditions (for example, a transfer voltage and a conveyance speed of the recording material at the time of transfer) and fixing conditions (for example, a fixing temperature and a conveyance speed of the recording material at the time of fixing) are controlled in accordance with a determination result.

Japanese Patent Laid-Open No. 2010-18433 describes an image forming apparatus provided with a grammage detection sensor configured to detect a grammage of a recording material by irradiating the recording material with an ultrasonic wave and receiving the ultrasonic wave that has attenuated via the recording material. In this image forming apparatus, image forming conditions such as transfer conditions and fixing conditions are controlled in accordance with the grammage of the recording material detected by the sensor. In addition, it is known that, in the above-described grammage detection sensor using the ultrasonic wave, the detection result varies depending on a surrounding environment where the sensor is installed (for example, a barometric pressure or a temperature). For that reason, according to Japanese Patent Laid-Open No. 2010-18433, by comparing a result of the reception of the ultrasonic wave in a state where the recording material does not exist with a result of the reception of the ultrasonic wave in a state where the recording material exists, an influence on the detection result by the change in the surrounding environment is suppressed.

However, the surrounding environment of the grammage detection sensor changes even in mid-course of image formation on plural sheets of the recording materials. In particular, in a case where the images are continuously formed on both surfaces of the plural sheets of the recording materials, the recording material that has once passed through a fixing device to be warmed up passes through in the vicinity of the sensor again, and therefore a temperature in the surrounding of the sensor is increased. When the temperature in the surrounding of the sensor is increased, the result of the ultrasonic wave reception is changed, and therefore the grammage of the recording material may be wrongly detected in some cases.

SUMMARY OF THE INVENTION

The present invention provides a grammage detection sensor that can accurately detect a grammage of a recording material irrespective of a change in a surrounding environment even in a case where images are continuously formed on plural sheets of the recording materials.

A grammage detection sensor according to an aspect of the present invention includes: a transmission unit configured to transmit an ultrasonic wave; a reception unit configured to receive the ultrasonic wave transmitted from the transmission unit; and a control unit configured to detect a grammage of a recording material, when a plurality of recording materials are continuously conveyed between the transmission unit and the reception unit, on the basis of a first ultrasonic wave received by the reception unit after the ultrasonic wave is transmitted by the transmission unit between a preceding recording material and a recording material following the preceding recording material, and a second ultrasonic wave received via a recording material by the reception unit after the ultrasonic wave is transmitted by the transmission unit.

Moreover, another embodiment provides an ultrasonic wave sensor that is used in an image forming apparatus having an image forming unit for forming an image on a recording material and a control unit for controlling an image forming condition of the image forming unit when an image is formed on the recording material. The ultrasonic wave sensor includes a transmission unit configured to transmit an ultrasonic wave; and a reception unit configured to receive the ultrasonic wave transmitted from the transmission unit. The control unit controls the image forming condition, the ultrasonic wave sensor outputs a first ultrasonic wave received not via the recording material by the reception unit after the ultrasonic wave is transmitted by the transmission unit, and a second ultrasonic wave received via the recording material by the reception unit after the ultrasonic wave is transmitted by the transmission unit to the control unit. In a case where a plurality of recording materials including a first recording material and a second recording material following the first recording material are continuously conveyed between the transmission unit and the reception unit, so that the control unit controls the image forming condition when an image is formed on the second recording material, the ultrasonic wave sensor outputs the first ultrasonic wave received by the reception unit between the first recording material and the second recording material, and the second ultrasonic wave received via the second recording material by the reception unit, to the control unit.

Moreover, in another embodiment the ultrasonic wave sensor previously obtains the first ultrasonic wave received by the reception unit in a first environment, and wherein in a case where the plurality of recording materials are continuously conveyed between the transmission unit and the reception unit in a second environment that is different from the first environment, so that the control unit controls the image forming condition when forming an image on the second recording material, the ultrasonic wave sensor outputs the first ultrasonic wave received by the reception unit in the first environment, the first ultrasonic wave received by the reception unit between the first recording material and the second recording material in the second environment, and the second ultrasonic wave received by the reception unit via the second recording material in the second environment, to the control unit.

Further features of the present invention will become apparent from the following description of exemplary embodiments with reference to the attached drawings.

BRIEF DESCRIPTION OF THE DRAWINGS

FIGS. 3A, 3B, and 3C illustrate examples of a drive signal and a reception waveform of the grammage detection sensor according to the exemplary embodiment of the present invention.

FIG. 4 illustrates an example of an output waveform of the grammage detection sensor according to the exemplary embodiment of the present invention.

FIGS. 7A and 7B are flow charts during the image-forming period according to a second exemplary embodiment of the present invention.

DESCRIPTION OF THE EMBODIMENTS

Hereinafter, embodiments of the present invention will be described with reference to the drawings. The following embodiments are merely examples and are not intended to limit the scope of this invention to those embodiments.

First Exemplary Embodiment

Figure 1:
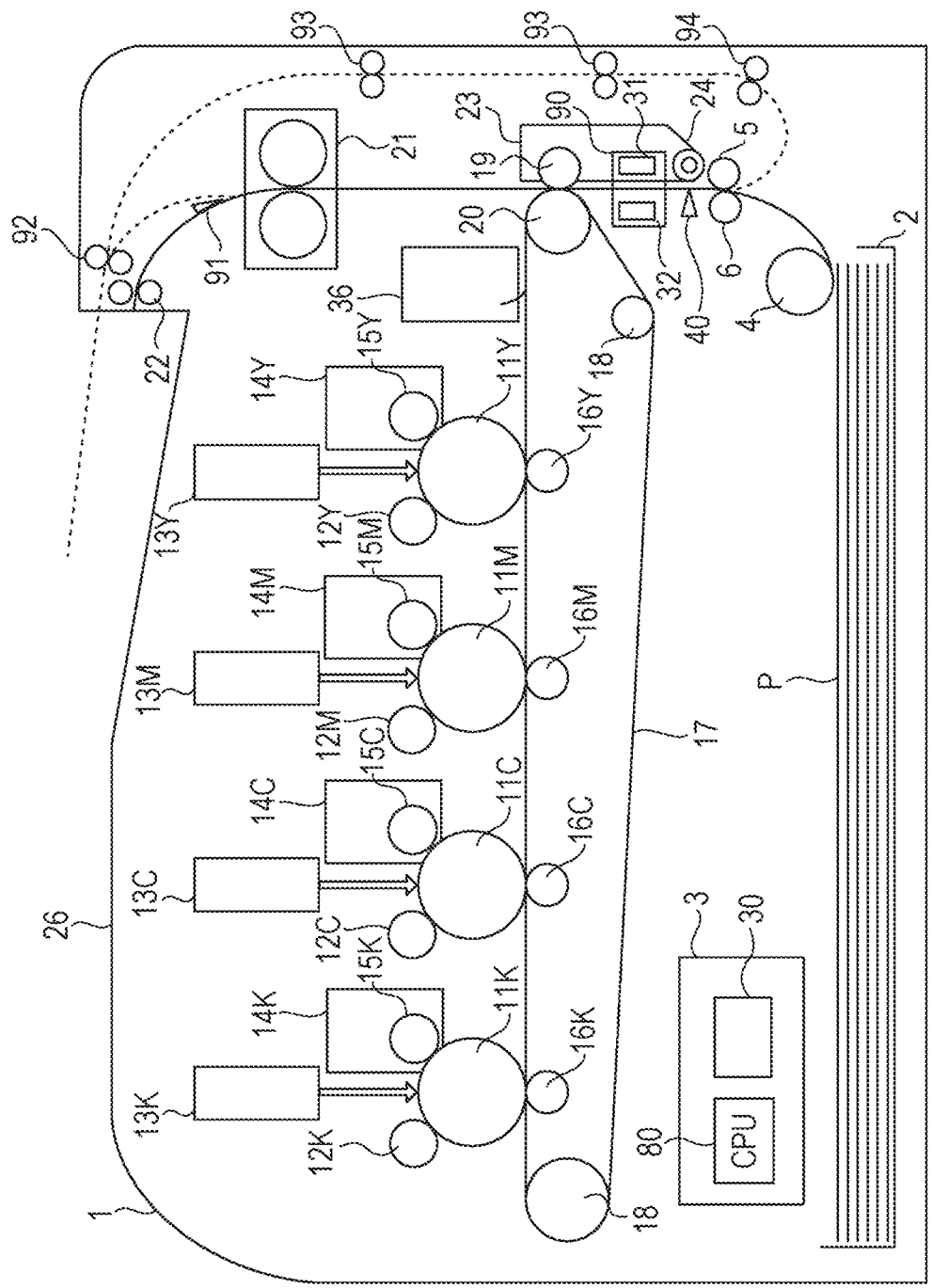
FIG. 1 is a block diagram illustrating a color image forming apparatus of a tandem system according to an exemplary embodiment of the present invention.

A grammage detection sensor according to the present exemplary embodiment can be used, for example, in an image forming apparatus such as a copier or a printer. FIG. 1 is a block diagram illustrating an image forming apparatus of a tandem system (four-drum system) that adopts an intermediate transfer belt, as an example of the image forming apparatus to which the grammage detection sensor is mounted.

An image forming apparatus 1 in FIG. 1 includes following configurations. A supply cassette 2 contains recording materials P. An image formation control unit 3 controls an operation of an image forming unit of the image forming apparatus 1. A supply roller 4 supplies the recording material P from the supply cassette 2. A conveying roller (conveyance unit) 5 conveys the recording material P supplied by the supply roller 4, and an opposing roller 6 (conveyance unit) for conveyance faces the conveying roller 5. Photosensitive drums 11Y, 11M, 11C, and 11K respectively bear developer (toner) of respective colors including yellow, magenta, cyan, and black. Charging rollers 12Y, 12M, 12C, and 12K for the respective colors uniformly charge the photosensitive drums 11Y, 11M, 11C, and 11K at a predetermined potential as primary charge members. Optical units 13Y, 13M, 13C, and 13K irradiate the photosensitive drums 11Y, 11M, 11C, and 11K charged by the primary charge members with laser light corresponding to image data of the respective colors to form electrostatic latent images. Developing units 14Y, 14M, 14C, and 14K visualize the electrostatic latent images formed on the photosensitive drums 11Y, 11M, 11C, and 11K. Developer conveying rollers 15Y, 15M, 15C, and 15K supply the developer in the developing units 14Y, 14M, 14C, and 14K to parts facing the photosensitive drums 11Y, 11M, 11C, and 11K. Primary transfer rollers (transfer units) 16Y, 16M, 16C, and 16K corresponding to the respective colors primarily transfer the images formed onto the photosensitive drums 11Y, 11M, 11C, and 11K. An intermediate transfer belt 17 bears the primarily transferred images. A driving roller 18 drives the intermediate transfer belt 17. A secondary transfer roller (transfer unit) 19 transfers the image formed on the intermediate transfer belt 17 to the conveyed recording material P, and an opposing roller 20 for secondary-transfer faces the secondary transfer roller 19. A fixing unit 21 fixes the image transferred to the recording material P while conveying the recording material P. A discharge roller 22 discharges the recording material P on which the fixing has been performed by the fixing unit 21 to an outside of the image forming apparatus 1. The image forming apparatus 1 also includes a flapper 91, a reversing roller 92, and duplex conveying rollers 93 and 94. A grammage detection sensor 90 includes a transmission unit 31 and a reception unit 32.

Next, an image forming operation of the image forming apparatus 1 will be described. A CPU 80 is mounted to the image formation control unit 3 and collectively controls the image forming operation of the image forming apparatus 1. An image formation command or image data is input to the image formation control unit 3 from a host computer or the like (not illustrated). Then, the image forming apparatus 1 starts the image forming operation, and the recording material P is supplied from the supply cassette 2 by the supply roller 4. The recording material P supplied from the supply cassette 2 by the supply roller 4 is conveyed by the conveying roller 5 and the opposing roller 6 for the conveyance and detected by a registration sensor 40. The recording material P detected by the registration sensor 40 is conveyed by the conveying roller 5 and the opposing roller 6 towards a nip portion (not illustrated) formed by the secondary transfer roller 19 and the opposing roller 20 for the secondary-transfer such that a timing is matched with the image formed on the intermediate transfer belt 17. Along with the operation of supplying the recording material P from the supply cassette 2, the photosensitive drums 11Y, 11M, 11C, and 11K are charged at a constant potential by the charging rollers 12Y, 12M, 12C, and 12K. Then, the optical units 13Y, 13M, 13C, and 13K expose surfaces of the charged photosensitive drums 11Y, 11M, 11C, and 11K with laser beam in accordance with the input image data to form electrostatic latent images. Development is performed by the developing units 14Y, 14M, 14C, and 14K and the developer conveying rollers 15Y, 15M, 15C, and 15K to visualize the formed electrostatic latent images. The electrostatic latent images formed on the surfaces of the photosensitive drums 11Y, 11M, 11C, and 11K are developed in the respective colors by the developing units 14Y, 14M, 14C, and 14K. Each of the photosensitive drums 11Y, 11M, 11C, and 11K is in contact with the intermediate transfer belt 17 and rotates in synchronism with the rotation of the intermediate transfer belt 17. The developed images in the respective colors are sequentially transferred onto the intermediate transfer belt 17 by the primary transfer rollers 16Y, 16M, 16C, and 16K. Then, the image formed on the intermediate transfer belt 17 is secondarily transferred onto the recording material P by the secondary transfer roller 19 and the opposing roller 20 for the secondary-transfer. The image transferred onto the recording material P is heated and pressurized to be fixed by the fixing unit 21 constituted by a fixing roller or the like. The developer remaining on the intermediate transfer belt 17 without being transferred onto the recording material P is cleaned by a cleaning unit 36.

In a case where the image formation is not performed on a back surface of the recording material P, the recording material P on which the image has been fixed is guided by the flapper 91 to a conveyance path where the discharge roller 22 is provided and is then discharged to a discharge tray 26. This conveyance path is indicated by a solid line in FIG. 1. On the other hand, in a case where the image formation is also performed on the back surface of the recording material P, the recording material P is guided by the flapper 91 to the conveyance path where the reversing roller 92 is provided. This conveyance path is indicated by a dotted line in FIG. 1. The reversing roller conveys the recording material P in a direction for discharging the recording material P to the outside and reversely rotates after a predetermined time elapses since the trailing edge of the recording material P (edge on an upstream side in the conveyance direction of the recording material P) passes through the flapper 91. The reversing roller 92 then conveys the recording material P to the duplex conveying roller 93. The duplex conveying roller 93 conveys the recording material P to the duplex conveying roller 94, and the recording material P temporarily stops at the duplex conveying roller 94. Thereafter, the recording material P is conveyed to the conveying roller 5 and the opposing roller 6 for the conveyance at a predetermined timing, and the image formation is similarly performed as in the front surface. When the images are continuously formed on both surfaces of the recording materials, the supply of the recording material by the supply roller 4 and the conveyance of the recording material by the duplex conveying roller 94 are alternately performed.

Next, the grammage detection sensor 90 will be described. A grammage mentioned herein is a mass per unit area of the recording material P, and the unit is represented by [g/m$^2$]. In the image forming apparatus 1 of FIG. 1, the grammage detection sensor 90 that detects the grammage of the recording material P is arranged on the upstream side in the conveyance direction of the recording material P with respect to the secondary transfer roller 19 and the opposing roller 20 for the secondary-transfer. The grammage detection sensor 90 includes the transmission unit configured to transmit an ultrasonic wave and the reception unit 32 configured to receive the ultrasonic wave, and the transmission unit 31 and the reception unit 32 are arranged so as to sandwich the conveyance path where the recording material P is conveyed. The transmission unit 31 is held by a secondary transfer unit 23 together with the secondary transfer roller 19. The secondary transfer unit can perform opening and closing operation while a rotating shaft 24 is set as a supporting point. Accordingly, even in a case where the conveyed recording material P is jammed in the vicinity of the secondary transfer unit 23, a user can easily remove the jammed recording material P. The image formation control unit 3 also includes a grammage detection sensor control unit 30 (hereinafter will be referred to as sensor control unit 30) configured to perform transmission and reception operations of the ultrasonic wave and a detection operation for the grammage of the recording material P in addition to the CPU 80. The CPU 80 controls various image forming conditions in accordance with a detection result of the grammage obtained by the sensor control unit 30. The image forming condition mentioned herein includes, for example, a conveyance speed of the recording material P, voltage values applied to the primary transfer rollers 16 and the secondary transfer roller 19, a temperature when the image is fixed on the recording material P by the fixing unit 21, or the like. Furthermore, the CPU 80 may control rotation speeds of the primary transfer rollers 16 and the secondary transfer roller 19 when the image is transferred as the image forming condition. Moreover, the CPU 80 may control a rotation speed of a fixing roller included in the fixing unit 21 when the image is fixed as the image forming condition.

The transmission unit 31 and the reception unit 32 have similar configurations and are constituted by a piezoelectric element corresponding to an inter-conversion element of a mechanical displacement and an electric signal, and an electrode terminal. In the transmission unit 31, when a pulse voltage at a predetermined frequency is input to the electrode terminal, the piezoelectric element oscillates, and an acoustic wave is generated. In a case where the recording material P exists in mid-course, the generated acoustic wave travels through the air and reaches the recording material P. When the acoustic wave reaches the recording material P, the recording material P oscillates by the acoustic wave. Since the recording material P oscillates, the acoustic wave is transmitted, and further, the acoustic wave travels through the air and reaches the reception unit 32. In this manner, the acoustic wave transmitted from the transmission unit 31 attenuates via the recording material P and reaches the reception unit 32. The piezoelectric element of the reception unit 32 outputs a voltage value in accordance with an amplitude of the received acoustic wave to the electrode terminal. This is the operation principle in a case where the ultrasonic wave is transmitted and received by using the piezoelectric elements.

Figure 2A:
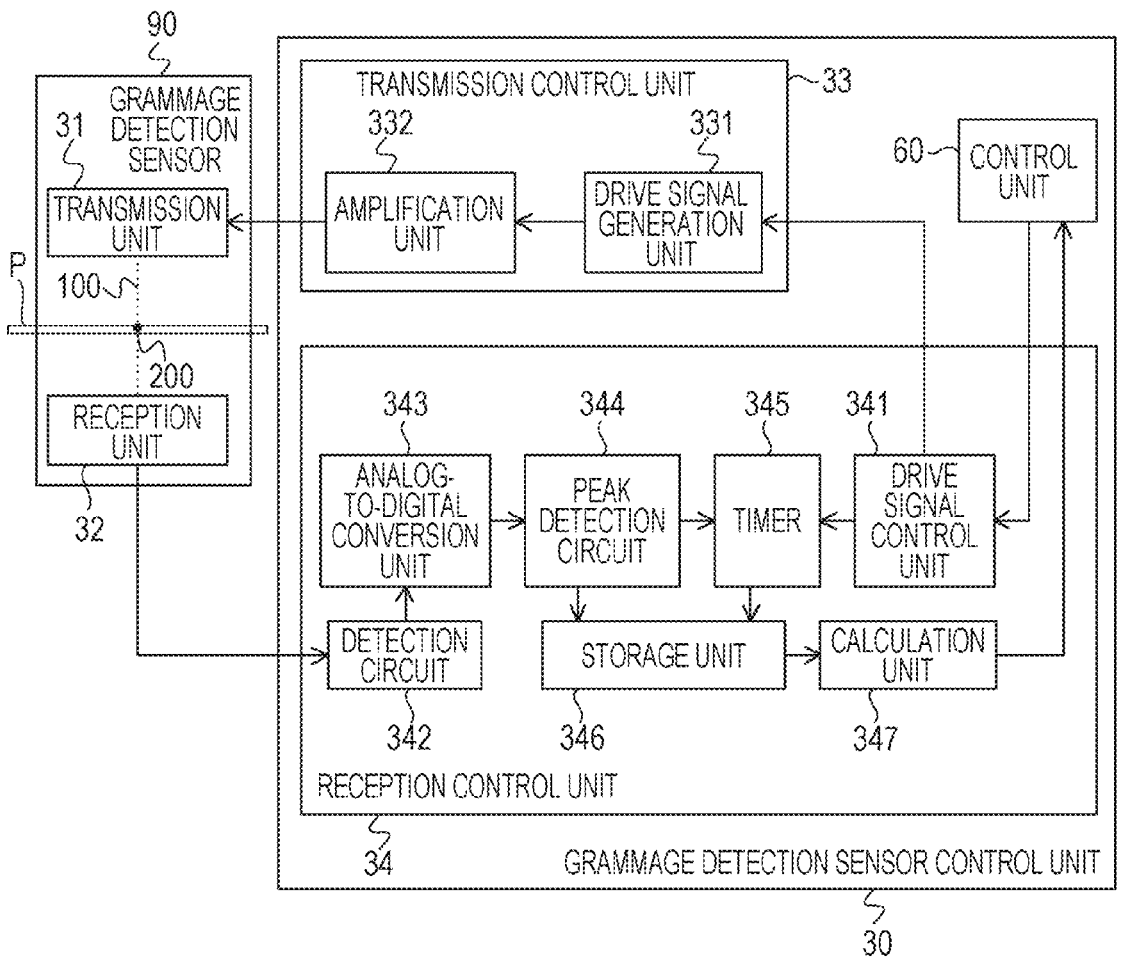
FIGS. 2A and 2B are block diagrams illustrating a configuration of a control unit in a grammage detection sensor according to the exemplary embodiment of the present invention.

Next, a detection method for the grammage of the recording material P by using the grammage detection sensor 90 will be described with reference to a block diagram of FIG. 2A. According to the present exemplary embodiment, the transmission unit 31 and the reception unit 32 transmit and receive the ultrasonic wave at a frequency of 32 kHz. The frequency of the ultrasonic wave is previously set, and a frequency in an appropriate range may be selected in accordance with the configurations of the transmission unit 31 and the reception unit 32, a detection accuracy, or the like. The sensor control unit 30 includes a transmission control unit 33 having functions of generate a drive signal for transmitting the ultrasonic wave and amplifying the drive signal and a reception control unit 34 having functions of detecting the ultrasonic wave received by the reception unit 32 as a voltage value and processing the signal. Furthermore, the sensor control unit 30 includes a control unit 60 configured to perform control of the respective units and detection of the grammage of the recording material P.

Figure 2B:
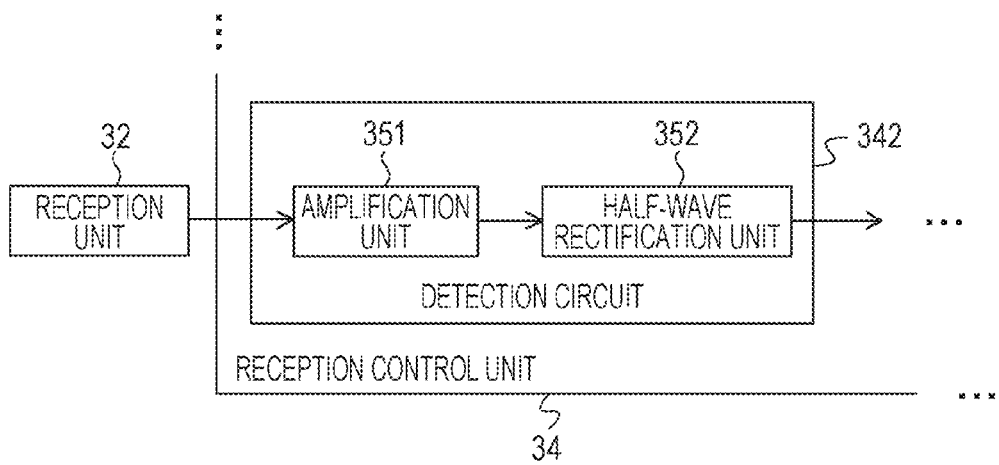

A signal indicating measurement start is input to a drive signal control unit 341 from the control unit 60. When the drive signal control unit 341 receives the input signal, the drive signal control unit 341 instructs a drive signal generation unit 331 to generate a drive signal to transmit an ultrasonic wave at a predetermined frequency. The drive signal generation unit 331 generates and outputs a signal having a previously set frequency. FIG. 3A illustrates a waveform of the drive signal generated by the drive signal generation unit 331. According to the present exemplary embodiment, pulse waves at 32 [kHz] are continuously output by five pulses in a single measurement. Then, the output of the pulse wave is paused for a predetermined time period, and the pulse wave is output again when the acoustic wave is completely attenuated to perform the next measurement. Accordingly, an influence of a disturbance such as a reflected wave or the like by the recording material P or a surrounding member is suppressed, so that only a direct wave emitted by the transmission unit 31 can be received by the reception unit 32. Such a signal is referred to as burst wave. An amplification unit 332 amplifies a level (voltage value) of the signal and outputs the signal to the transmission unit 31. The reception unit receives the ultrasonic wave transmitted from the transmission unit 31 or the ultrasonic wave attenuated via the recording material P and outputs the received signal to a detection circuit 342 of the reception control unit 34. As illustrated in FIG. 2B, the detection circuit 342 includes an amplification unit 351 and a half-wave rectification unit 352. According to the present exemplary embodiment, the amplification unit 351 can vary an amplification factor of the received signal in a state where the recording material P does not exist in a detection position 200 between the transmission unit 31 and the reception unit 32 and in a state where the recording material P exists in the detection position 200. Herein, the detection position 200 refers to a virtual position existing in a region where the recording material P is conveyed and a position where the ultrasonic wave transmitted from the transmission unit 31 is emitted. When the recording material P is conveyed to the detection position 200, the ultrasonic wave transmitted from the transmission unit 31 reaches the recording material P. Then, the reception unit 32 can receive the ultrasonic wave attenuated via the recording material P. For example, as illustrated in FIGS. 2A and 2B, a position where a virtual line 100 that connects a center of the transmission unit 31 to a center of the reception unit 32 intersects with the region where the recording material P is conveyed can be set as the detection position 200. The recording material P is conveyed by the conveying roller 5 and the opposing roller 6 for the conveyance to the detection position 200. The half-wave rectification unit 352 performs half-wave rectification with respect to the signal amplified in the amplification unit 351. However, the respective configurations are not limited to the above. FIG. 3B illustrates a waveform of the received signal in the reception unit 32, and FIG. 3C illustrates a waveform of the signal after the half-wave rectification. The signal generated by the detection circuit 342 is converted from an analog signal to a digital signal by an analog-to-digital conversion unit 343. A peak detection unit 344 detects a peak value (local maximum value) of the signal on the basis of the converted digital signal. In a timer 345, counting is started at a timing when the drive signal control unit 341 instructs the generation of the drive signal, and the peak detection unit 344 measures a time period until when the peak value is detected. Then, the value detected by the peak detection unit 344 and the time period measured by the timer 345 are both saved in a storage unit 346. The above-described operation is referred to as "peak detection operation". The peak detection operation is executed predetermined times respectively in predetermined intervals in the state where the recording material P does not exist in the detection position 200 between the transmission unit 31 and the reception unit 32 and in the state where the recording material P exists in the detection position 200. A calculation unit 347 calculates a calculation coefficient from a ratio of an average value of the peak values for the predetermined times in the state where the recording material P does not exist in the detection position 200 to an average value of the peak values for the predetermined times in the state where the recording material P exists in the detection position 200. The calculation coefficient is a value equivalent to a grammage, and the control unit 60 detects the grammage of the recording material P on the basis of the calculation coefficient calculated by the calculation unit 347. The CPU 80 controls the image forming condition of the image forming apparatus 1 on the basis of the detection result for the grammage. In addition, the CPU 80 may also directly control the image forming condition of the image forming apparatus 1 from the value of the calculation coefficient without detecting the grammage of the recording material P by the control unit 60.

Subsequently, the peak detection operation will be described in detail. FIG. 4 illustrates a waveform of the received signal of the recording material P according to the present exemplary embodiment. The used recording material P is recording paper having a grammage of 60 [g/m²] (hereinafter, will be simply referred to as paper). An axis of abscissa indicates a counter value equivalent to an elapsed time since the ultrasonic wave is transmitted from the transmission unit 31, and an axis of ordinate indicates an output value equivalent to an amplitude of the ultrasonic wave. According to the present exemplary embodiment, a counter frequency of the timer 345 is 3 [MHz] (0.333 [μsec] interval), and a resolution of the peak detection unit 344 is 3.3 [V] (0.806 [mV] interval) of AD 12 bits. In addition, in order to obtain stable data even in the state where the paper exists in the detection position 200 between the transmission unit 31 and the reception unit 32, the amplification factor of the detection circuit 342 in the state where the paper exists in the detection position 200 is set as ×16. A waveform indicated by a solid line and a waveform indicated by a dotted line respectively indicates a waveform when the paper is absent and a waveform when the paper is present. Hereinafter, the "paper absent" state indicates a state where the paper does not exist in the detection position 200 between the transmission unit 31 and the reception unit 32, and the "paper present" state indicates a state where the paper exists in the detection position 200 between the transmission unit 31 and the reception unit 32. In FIG. 4, a reason why the peak value periodically appears is that the burst wave is input. In addition, a reason why the timing of detecting the peak value varies depending on the presence or absence of the paper is that the ultrasonic wave attenuates because of the presence of the paper, and the speed of the ultrasonic wave is decreased. As illustrated in FIG. 4, values of the first two peak values (n=1 and 2 in the drawing) are low, and the stable peak values may not be obtained depending on the presence or absence of the paper or the type in some cases. On the other hand, the influence of the disturbance such as the reflected wave occurs when a predetermined time elapses since the ultrasonic wave is transmitted, and the peak value is thus preferably obtained as early as possible within a range where a necessary amplitude can be obtained. Therefore, according to the present exemplary embodiment, the grammage detection is performed by using the peak value of n=3 in FIG. 4.

Figure 5A:
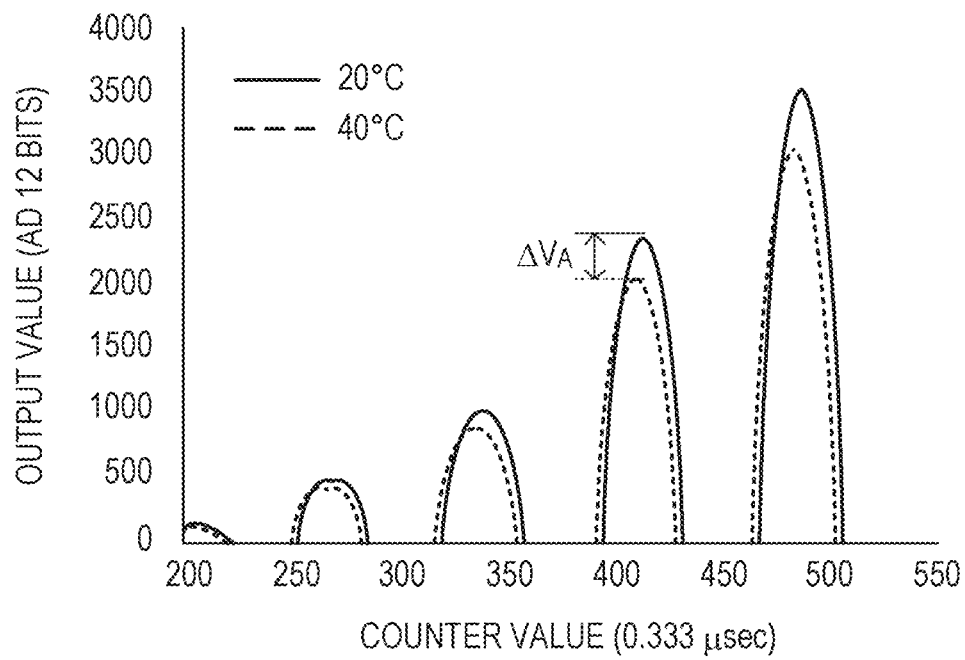
FIGS. 5A and 5B illustrate an influence on a grammage detection accuracy by a change in a surrounding temperature according to the exemplary embodiment of the present invention.
Figure 5B:
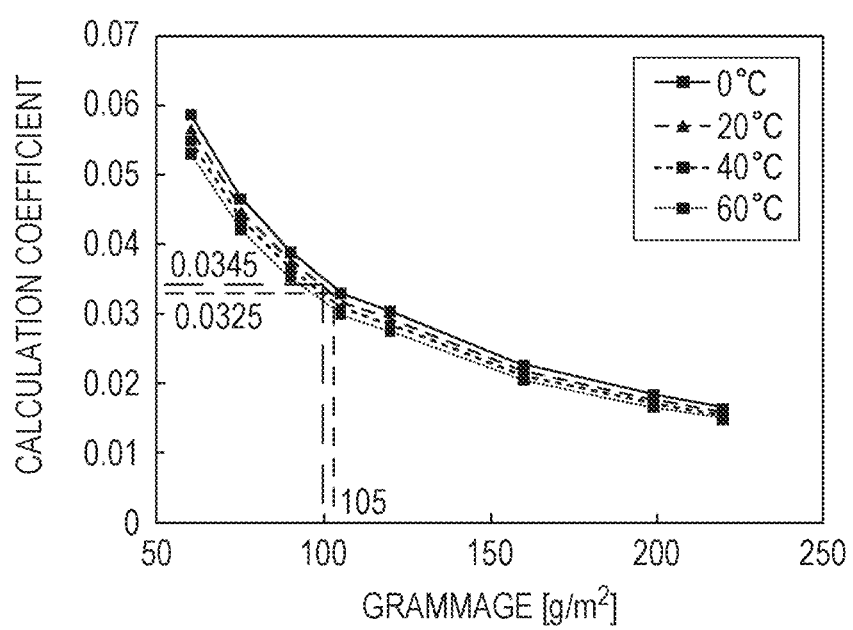

Next, an influence on a detection accuracy for the grammage by a surrounding environment (for example, a barometric pressure or a temperature) of the sensor and a correction method will be described. First, the influence by the change in the surrounding temperature will be described by using FIGS. 5A and 5B. FIG. 5A illustrates an output value of the ultrasonic wave received by the reception unit 32 when the paper is absent. A solid line indicates an output value of the ultrasonic wave when the surrounding temperature is 20° C., and a dotted line indicates an output value of the ultrasonic wave when the surrounding temperature is 40° C. Each of the output values is measured while the surrounding temperature is changed under a condition where the level of the drive signal of the transmission unit 31 and the barometric pressure in the surrounding of the sensor are the same. As the surrounding temperature is higher, the detected value of the peak value is lower. In general, an acoustic velocity v propagating through the air is represented as v=331.5+0.607 k [m/s] (k: Celsius temperature [° C.]), and as the surrounding temperature is higher, the acoustic velocity v is increased. Therefore, the output value of the ultrasonic wave when the surrounding temperature is 40° C. changes faster than that when the surrounding temperature is 20° C. Subsequently, the influence on the detection accuracy for the grammage by the change in the surrounding temperature will be described by using FIG. 5B. An axis of abscissa indicates a grammage of the paper, and an axis of ordinate indicates a calculation coefficient. When the peak value when the paper is present is set as Vp, and the peak value when the paper is absent is set as Va, a calculation coefficient τ is represented as Expression (1).

$$\tau = Vp/Va \qquad \text{Expression (1)}$$

Herein, the peak value Vp when the paper is present and the peak value Va when the paper is absent are respectively detected in states where the surrounding temperature is changed (0° C., 20° C., 40° C., and 60° C.). First, a reason why the calculation coefficient τ described above is obtained will be described. In a manufacturing process of the grammage detection sensor 90, the positions of the transmission unit 31 and the reception unit 32 may be fluctuated with respect to the recording material P corresponding to the detection target. In addition, when the grammage detection sensor 90 is mounted to a main body of the apparatus too, the positions of the transmission unit 31 and the reception unit 32 may be fluctuated in some cases. When the positions of the transmission unit 31 and the reception unit 32 are changed, the peak value or the like output from the reception unit 32 is changed. In the above-described case, if the grammage of the recording material P is detected only from the peak value Vp when the paper is present, different detection results for the grammage may be output from different sensors even when the same recording material P is detected. For that reason, while the calculation coefficient τ is obtained and compared with the peak value when the paper is absent which has been detected by the same sensor, the influence by the position of the sensor is suppressed. Considerations will be given of a case where the grammage of the paper is detected by using this calculation coefficient when the surrounding temperature is changed.

For example, the grammage of the paper where the calculation coefficient τ indicates a value of 0.0325 in an environment having a surrounding temperature of 40° C. is detected as 100 [g/m²]. On the other hand, the grammage of the paper where the calculation coefficient τ indicates a value of 0.0325 in an environment having the surrounding temperature of 20° C. is detected as 105 [g/m²]. For that reason, if the correction is not performed in accordance with the surrounding temperature, the paper having the grammage of 100 [g/m²] is wrongly detected as the paper having the grammage of 105 [g/m²]. In this manner, a reason why the grammage detection sensor 90 functioning as the ultrasonic wave sensor is affected by the change in the surrounding temperature is related to an air density. For example, when the temperature in the surrounding of the sensor is increased, the air expands to decrease the air density, and it becomes more difficult for the ultrasonic wave to transmit. On the other hand, when the temperature is decreased, the air contracts to increase the air density, and it becomes easier for the ultrasonic wave to transmit. That is, a difficulty for the transmission of the sound (acoustic impedance) is changed by the surrounding temperature.

Figure 8:
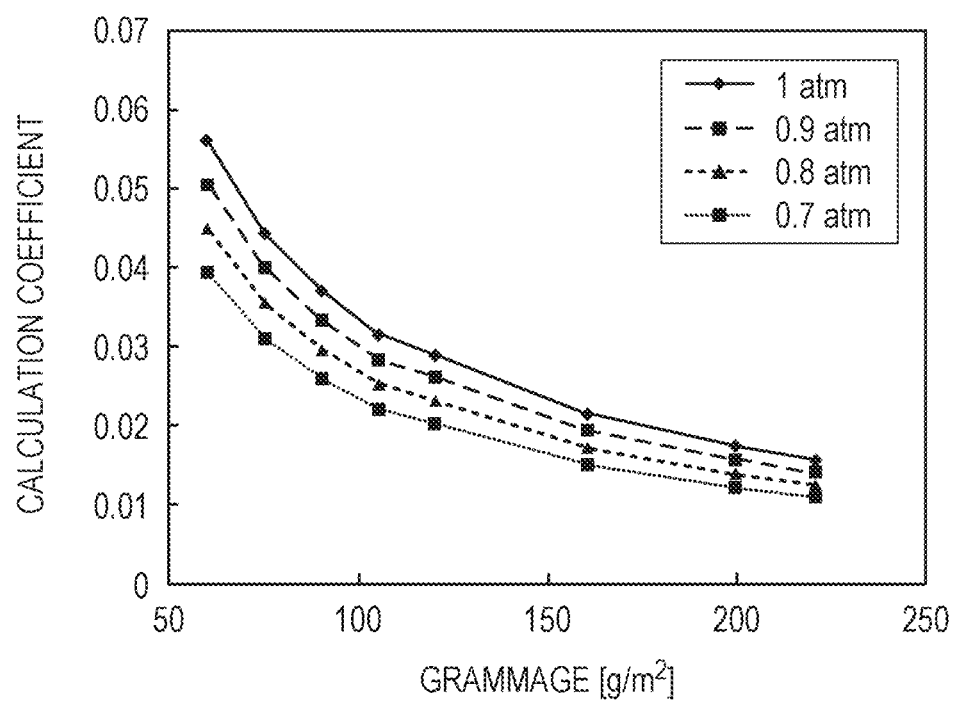
FIG. 8 illustrates an influence on the grammage detection accuracy by the change in the surrounding temperature according to the exemplary embodiment of the present invention.

A change in the acoustic impedance also occurs in a case where the surrounding barometric pressure is changed. FIG. 8 is an explanatory diagram for the influence on the detection accuracy for the grammage by the change in the barometric pressure when the surrounding temperature is 20° C. An axis of abscissa indicates a grammage of the paper, and an axis of ordinate indicates a calculation coefficient. As the barometric pressure is lower, the calculation coefficient is decreased. Herein, both the peak value Vp when the paper is present and the peak value Va when the paper is absent are detected in states where the surrounding barometric pressure is changed (1 [atm], 0.9 [atm], 0.8 [atm], and 0.7 [atm]). In this manner, a reason why the grammage detection sensor 90 functioning as the ultrasonic wave sensor is affected by a change in the surrounding barometric pressure is similarly related to the air density as in the case of the temperature. For example, when the barometric pressure in the surrounding of the sensor is increased, the air contracts to increase the air density, and it becomes easier for the ultrasonic wave to transmit. On the other hand, when the barometric pressure is decreased, the air expands to decrease the air density, and it becomes more difficult for the ultrasonic wave to transmit.

Since an output of the grammage detection sensor functioning as the ultrasonic wave sensor is proportional to the acoustic impedance, the change in the surrounding environment can be detected and corrected from the ratio of the output values before and after the surrounding environment is changed. As a specific method, first, the detection is performed in the state where the paper is absent in an environment where the surrounding barometric pressure or the temperature is previously found such as a time of factory shipment, and the measured peak value is stored in the storage unit 346 or the like as a reference peak value. According to the present exemplary embodiment, the environment where the reference peak value is measured is set as 20° C. and 1 [atm]. Next, when the surrounding environment may be changed after the shipment, the detection is similarly performed in the state where the paper is absent. While a ratio of the measured peak value to the reference peak value is set as a correction coefficient, it is possible to correct the calculation coefficient. This calculation coefficient is set as environment correction coefficient α. When the paper absent peak value functioning as a reference is set as Va0, the environment correction coefficient α is represented as follows.

$$\alpha = Va/Va0 \qquad \text{Expression (2)}$$

The calculation coefficient τr at 20° C. and 1 [atm] is represented by the following expression.

$$\tau r = \tau/\alpha \qquad \text{Expression (3)}$$

In this manner, with the application of the correction by the environment correction coefficient α, the calculation coefficient at 20° C. and 1 atm can be obtained irrespective of the change in the surrounding environment, and the accurate grammage can be detected.

Figure 6A:
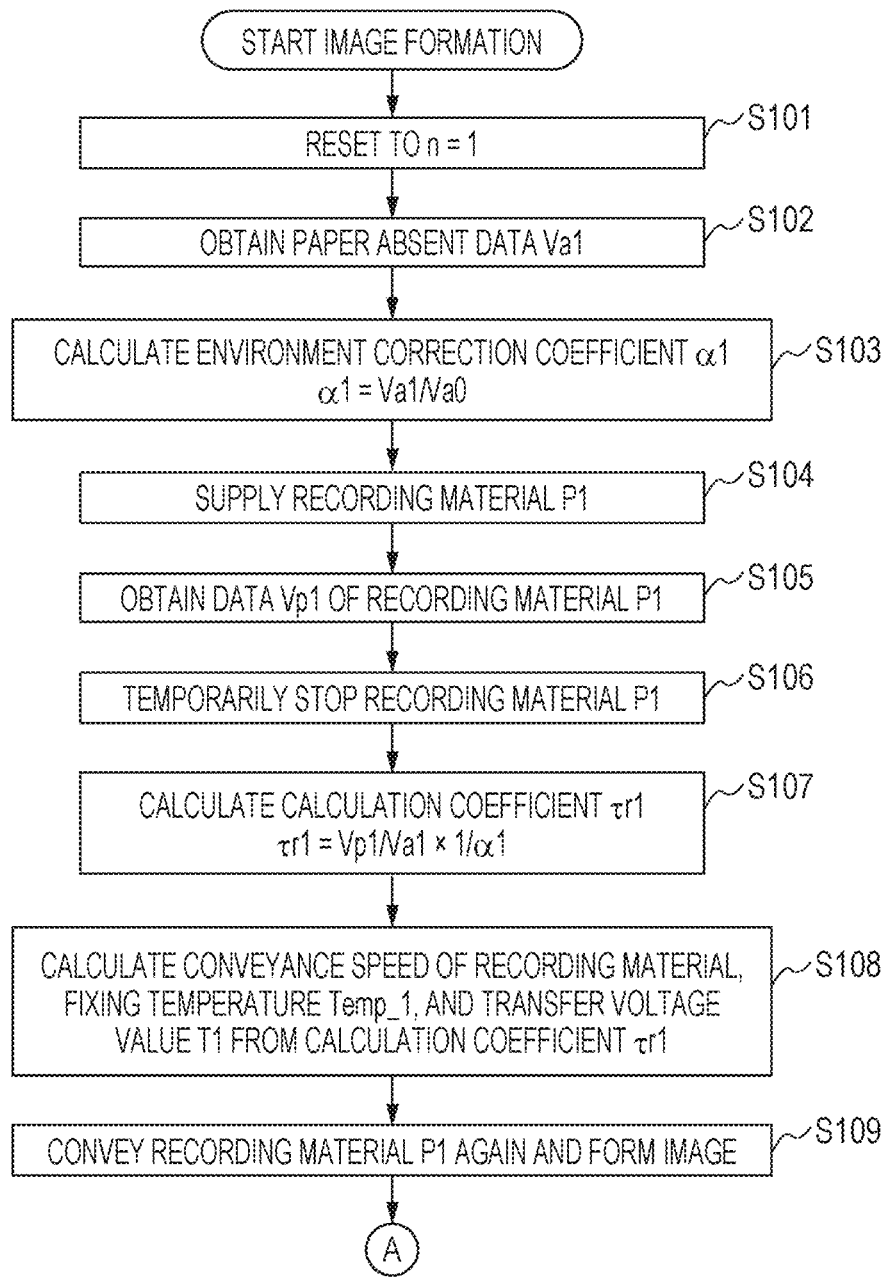
FIGS. 6A and 6B are flow charts during an image-forming period according to a first exemplary embodiment of the present invention.
Figure 6B:
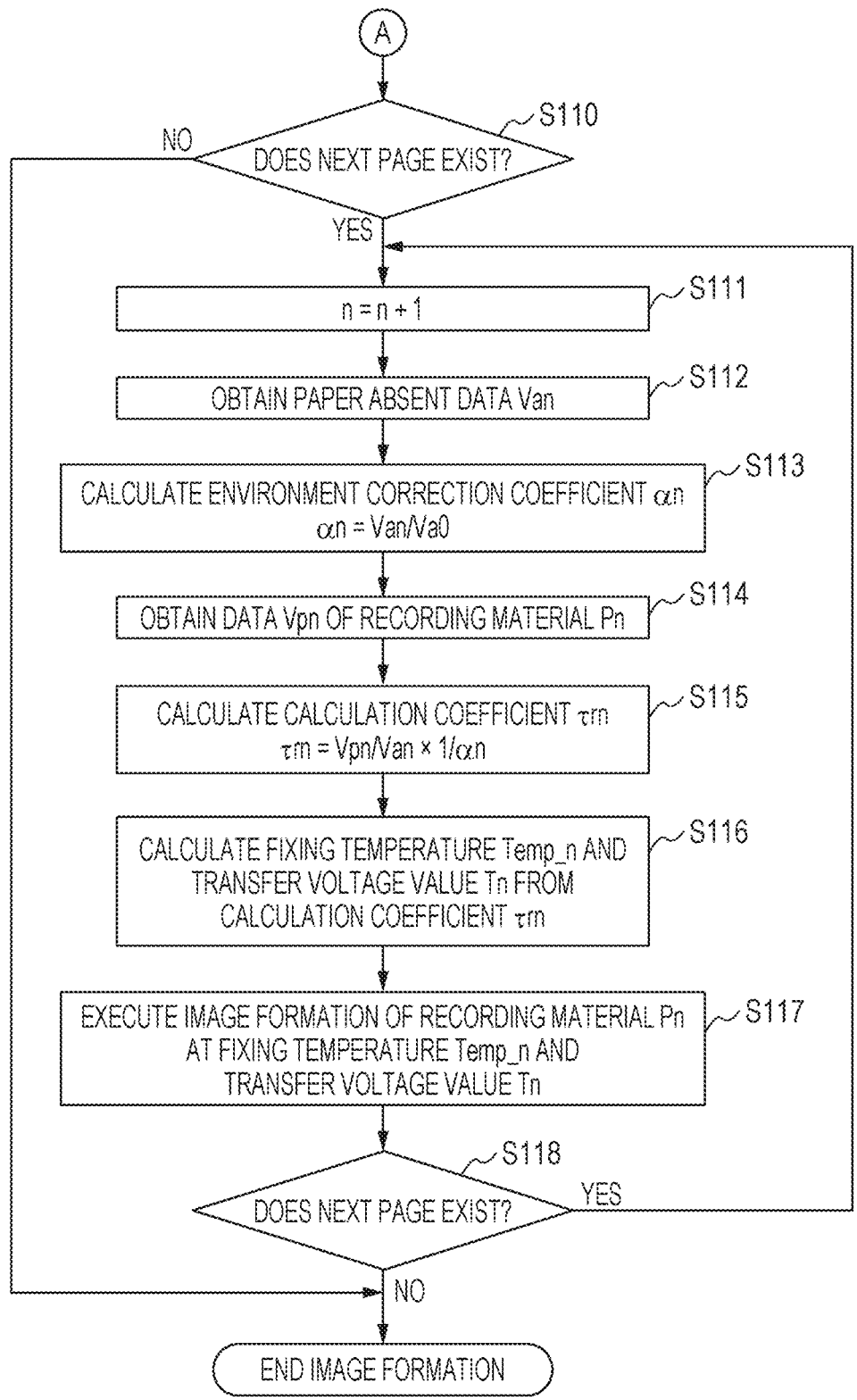

Next, an image forming method according to the present exemplary embodiment will be described by using flow charts of FIGS. 6A and 6B. It is noted that a case where images are continuously formed on the plural sheets of the recording materials P will be described hereafter. According to the present exemplary embodiment, the case where the images are continuously formed on the plural sheets of the recording materials P refers to a case where the user issues a command to cause the image forming apparatus 1 to form the images on the plural sheets of the recording materials P. A recording material P1 indicates a first sheet, a recording material P2 indicates a second sheet, and a recording material Pn indicates an n-th sheet. A control based on the flow charts of FIGS. 6A and 6B is executed by the CPU 80 or the like on the basis of a program stored in a ROM (not illustrated). In addition, according to the present exemplary embodiment, paper is used as the recording material.

The CPU 80 first resets the sheet number n to 1 after the image formation is started (S101). Subsequently, the grammage detection sensor 90 obtains the peak value by the above-described peak detection operation in the state where the paper is absent. According to the present exemplary embodiment, the peak detection operation is performed 20 times at 10 ms intervals, and an average value is set as a paper absent data Va1 (S102). Next, the paper absent data Va1 is divided by the reference data Va0 at the time of the factory shipment which is stored in the storage unit 346 to calculate the environment correction coefficient α1 (S103). Subsequently, the CPU 80 supplies the recording material P1 from the supply cassette 2 (S104) and obtains the paper present data by performing the peak detection operation at a predetermined timing after the recording material P1 has reached the grammage detection sensor 90. In more detail, the peak detection operation is performed during a period from when a leading edge of the recording material P1 (edge part on the downstream side in the conveyance direction of the recording material P1) passes through the detection position 200 between the transmission unit 31 and the reception unit 32 until when the trailing edge of the recording material P1 reaches the detection position 200. According to the present exemplary embodiment, the peak detection operation is performed 20 times at 10 ms intervals similarly as in S102, and the average value is set as the paper present data Vp1 (S105). Thereafter, the CPU 80 temporarily stops the recording material P1 (S106). Subsequently, a calculation coefficient $\tau r1$ normalized at 20° C. and 1 [atm] by using Expression (4) is calculated (S107), and a conveyance speed of the recording material, a fixing temperature Temp_1, and a transfer voltage value T1 are calculated from the calculated calculation coefficient $\tau r1$ (S108). It is noted that according to the present exemplary embodiment, the recording material P1 is temporarily stopped to be ready for coping with a case where the conveyance speed of the recording material P1 is changed.

$$\tau r1 = Vp1/Va1 \times 1/\alpha1 \quad \text{Expression (4)}$$

After the conditions are changed to the calculated conveyance speed, the fixing temperature, and the transfer voltage value, the CPU 80 conveys the recording material P1 again to perform the image formation (S109). The CPU 80 checks the presence or absence of the following recording material in parallel with the image forming operation in S109 (S110). In a case where the following recording material is absent, the image formation is ended for no further operation. On the other hand, in a case where the following recording material is present, the sheet number n is incremented (S111). The peak detection operation is performed during a period from when the recording material Pn−1 passes through the grammage detection sensor 90 until when the following recording material Pn reaches (hereinafter, will be referred to as paper absent period). In more detail, the peak detection operation is performed during the time period from when the trailing edge of the recording material Pn−1 passes through the detection position 200 between the transmission unit 31 and the reception unit 32 until when the leading edge of the recording material Pn reaches the detection position 200. According to the present exemplary embodiment, by calculating the average value by performing the peak detection operation 10 times at 10 ms intervals, the paper absent data Van is obtained during the paper absent period (S112). Next, the environment correction coefficient $\alpha n$ is calculated by diving the paper absent data Van by the reference data Va0 at the time of the factory shipment which is stored in the storage unit 346 (S113). The peak detection operation is performed at a predetermined timing after the recording material Pn reaches the grammage detection sensor 90 to obtain the paper present data. In more detail, the peak detection operation is performed during the time period from when the leading edge of the recording material Pn passes the detection position 200 between the transmission unit 31 and the reception unit 32 until when the trailing edge of the recording material Pn reaches the detection position 200. According to the present exemplary embodiment, the peak detection operation is similarly performed 20 times at 10 ms intervals as in S105, and the average value is set as the paper present data Vpn (S114). Subsequently, a calculation coefficient $\tau rn$ normalized at 20° C. and 1 [atm] is calculated by using Expression (5) (S115), and a fixing temperature Temp_n and a transfer voltage value Tn are calculated from the calculated calculation coefficient $\tau rn$ (S116).

$$\tau rn = Vpn/Van \times 1/\alpha n \quad \text{Expression (5)}$$

After the trailing edge of the recording material Pn−1 passes through the fixing unit 21, the CPU 80 changes the fixing temperature to Temp_n and changes the transfer voltage value to Tn to perform the image formation (S117). The CPU 80 checks the presence or absence of the following recording material in parallel with the image forming operation in S117 (S118). In a case where the following recording material is absent, the image formation is ended for no further operation. On the other hand, in a case where the following recording material is present, the flow returns to S111, and the image formation is continued until when the following recording material becomes absent.

In a case where the images are continuously formed on the plural sheets of the recording materials by performing the above-described operation, even when the surrounding environment is changed, it is possible to accurately detect the grammage of the recording material. In addition, it is possible to set the image forming conditions such as the optimal transfer condition and fixing condition for the second and subsequent recording materials.

In particular, even if the temperature in the surrounding of the grammage detection sensor 90 is increased when the images are continuously formed on both sides of the plural sheets of the recording materials, it is possible to accurately detect the grammage of the recording material.

In addition, according to the present exemplary embodiment, the environment correction coefficient $\alpha n$ is calculated by comparing the data Van detected during the paper absent period between the trailing edge of the recording material Pn−1 and the leading edge of the recording material Pn with the reference paper absent data Va0. However, the configuration is not limited to the above. A table in which the paper absent data Van and the environment correction coefficient $\alpha n$ are associated with each other is previously stored in the storage unit 346, and the environment correction coefficient $\alpha n$ may be directly obtained from the paper absent data Van on the basis of the table. This table is set at the time of the factory shipment or the like in accordance with the configuration of the grammage detection sensor 90. In addition, the correspondence relationship between Van and $\alpha n$ is set while a case where the environment correction coefficient is set as 1 with respect to the reference paper absent data Va0 is used as a reference.

Second Exemplary Embodiment

According to the first exemplary embodiment, the configuration has been described in which the paper absent data Van during the paper absent period is obtained by calculating the average value by performing the peak detection operation 10 times at 10 ms intervals. However, in a case where the paper absent period is short, the peak detection operation may not be performed 10 times in some cases. According to the present exemplary embodiment, the case where the paper absent period is short is supposed, and a configuration in which the peak detection operation can be executed only up to 3 times during the paper absent period will be described. Descriptions on main parts are similar to the first exemplary embodiment, and only parts different from the first exemplary embodiment will be described here.

Figure 7B:
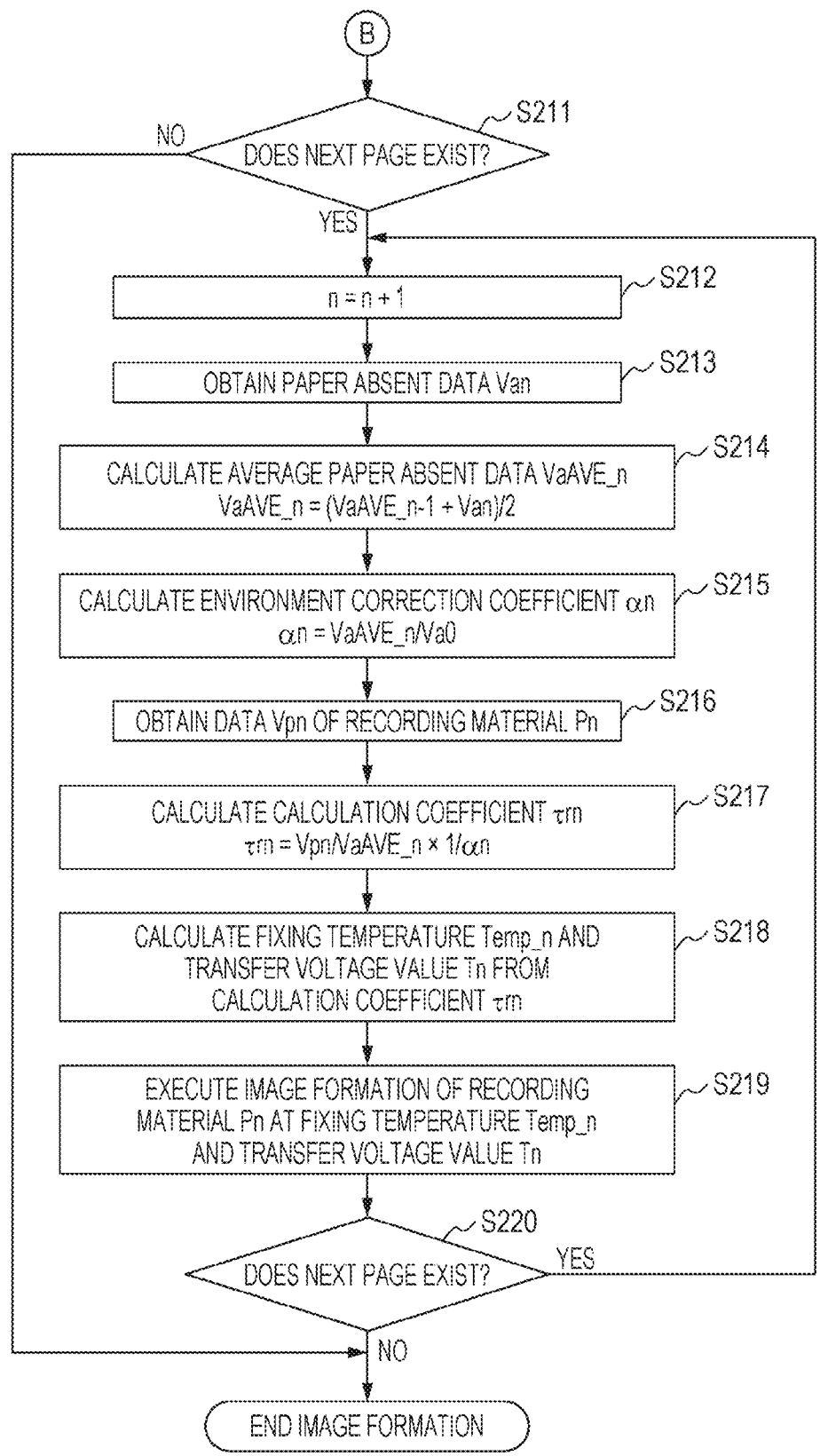

The image forming operation according to the present exemplary embodiment will be described by using flow charts of FIGS. 7A and 7B. A control based on the flow charts of FIGS. 7A and 7B is executed by the CPU 80 or the like on the basis of the program stored in the ROM (not illustrated).

The CPU 80 first resets the sheet number n to 1 after the image formation is started (S201). Subsequently, the grammage detection sensor 90 obtains the peak value by the above-described peak detection operation in the state where the paper is absent. According to the present exemplary embodiment, the peak detection operation is performed 20 times at 10 ms intervals, and the average value is set as the paper absent data Va1 (S202). Va1 is saved in the storage unit 346 as VaAVE_1 (S203). Next, the paper absent data Va1 is divided by the reference data Va0 at the time of the factory shipment which is stored in the storage unit 346 to calculate the environment correction coefficient α1 (S204). Subsequently, the CPU 80 supplies the recording material P1 from the supply cassette 2 (S205) and obtains the paper present data by performing the peak detection operation at a predetermined timing after the recording material P1 has reached the grammage detection sensor 90. In more detail, the peak detection operation is performed during a period from when the leading edge of the recording material P1 passes through the detection position 200 between the transmission unit 31 and the reception unit 32 until when the trailing edge of the recording material P1 reaches the detection position 200. According to the present exemplary embodiment, the peak detection operation is performed 20 times at 10 ms intervals similarly as in S202, and the average value is set as the paper present data Vp1 (S206). Thereafter, the CPU 80 temporarily stops the recording material P1 (S207). Subsequently, the calculation coefficient τr1 normalized at 20° C. and 1 [atm] is calculated by using Expression (6) (S208), and the conveyance speed of the recording material, the fixing temperature Temp_1, and the transfer voltage value T1 are calculated from the calculated calculation coefficient τr1 (S209).

$$\tau r1 = Vp1/Va1 \times 1/\alpha 1 \qquad \text{Expression (6)}$$

After the conditions are changed to the calculated conveyance speed of the recording material, the fixing temperature, and the transfer voltage value, the CPU 80 conveys the recording material P1 again to perform the image formation (S210). The CPU 80 checks the presence or absence of the following recording material in parallel with the image forming operation in S210 (S211). In a case where the following recording material is absent, the image formation is ended for no further operation. On the other hand, in a case where the following recording material is present, the sheet number n is incremented (S212), and the peak detection operation is performed during the paper absent period. In more detail, the peak detection operation is performed during the period from when the trailing edge of the recording material Pn−1 passes through the detection position 200 between the transmission unit 31 and the reception unit 32 until when the leading edge of the recording material Pn reaches the detection position 200. According to the present exemplary embodiment, the peak detection operation is performed 3 times at 10 ms intervals to calculate the average value to obtain the paper absent data Van (S213). Next, the paper absent data VaAVE_n is calculated by using Expression (7) (S214).

$$VaAVE\_n = (VaAVE\_n-1 + Van)/2 \qquad \text{Expression (7)}$$

Next, the environment correction coefficient αn is calculated by dividing the paper absent data VaAVE_n by the reference data Va0 at the time of the factory shipment stored in the storage unit 346 (S215). The peak detection operation is performed at a predetermined timing after the recording material Pn reaches the grammage detection sensor 90 to obtain the paper present data. In more detail, the peak detection operation is performed during the period from when the leading edge of the recording material Pn passes the detection position 200 between the transmission unit 31 and the reception unit 32 until when the trailing edge of the recording material Pn reaches the detection position 200. According to the present exemplary embodiment, the peak detection operation is similarly performed 20 times at 10 ms intervals as in S205, and the average value is set as the paper present data Vpn (S216). Subsequently, the calculation coefficient τrn normalized at 20° C. and 1 [atm] is calculated by using Expression (8) (S217), and the fixing temperature Temp_n and the transfer voltage value Tn are calculated from the calculated calculation coefficient τrn (S218).

$$\tau rn = Vpn/VaAVE\_n \times 1/\alpha n \qquad \text{Expression (8)}$$

After the trailing edge of the recording material Pn−1 passes through the fixing unit 21, the CPU 80 changes the fixing temperature to Temp_n and changes the transfer voltage value to Tn to perform the image formation (S219). The CPU 80 checks the presence or absence of the following recording material in parallel with the image forming operation in S219 (S220). In a case where the following recording material is absent, the image formation is ended for no further operation. On the other hand, in a case where the following recording material is present, the flow returns to S212, and the image formation is continued until when the following recording material becomes absent.

When the above-described operation is performed, even in a case where the sufficient paper absent data cannot be obtained in the single paper absent period because the paper absent period is short, it is possible to accurately detect the grammage of the recording material. In addition, it is possible to set the image forming conditions such as the optimal transfer condition and fixing condition for the second and subsequent recording materials.

In addition, the calculation expression for calculating VaAVE_n is not limited to Expression (7) according to the present exemplary embodiment. As illustrated in Expression (9), a weighting average value in accordance with the number of pieces of data may be calculated.

$$VaAVE\_n = (n1 \times VaAVE\_n-1 + n2 \times Van)/(n1+n2) \qquad \text{Expression (9)}$$

Where, in Expression (9), n1 denotes the number of pieces of data obtained by performing the peak detection operation by the time when the previous paper absent data VaAVE_n−1 is obtained. In addition, n2 denotes the number of pieces of data obtained by performing the peak detection operation this time. For example, n=2 is assigned to Expression (9), and VaAVE_2=(n1×VaAVE_1+n2×Va2)/(n1+n2)=(20×Va1+3×Va2)/23 is established.

Thus, it is possible to calculate the number of pieces of data in accordance with the accurate paper absent data.

Third Exemplary Embodiment

According to the first exemplary embodiment and the second exemplary embodiment, the data obtainment in the reference environment and the environment when the grammage detection is performed is performed in a state where the pulse voltages input to the transmission unit 31 are equal to each other. Then, the grammage calculation is performed while a ratio of the paper absent peak values in the respective environments is set as the environment correction coefficient α. According to the present exemplary embodiment, a method of correcting the influence by the change in the surrounding environment by changing the pulse voltage of the drive signal in accordance with the surrounding environment will be described. Descriptions on main parts are similar to the first exemplary embodiment, and only parts different from the first exemplary embodiment will be described here.

First, a reference paper absent peak value obtained by an input pulse voltage Vi0 under the reference environment is set as Va0. Then, a paper absent peak value obtained by the input pulse voltage Vi0 under the environment at the time of the grammage detection is set as Va1. The sensor control unit 30 adjusts the input pulse voltage such that the value Va of the obtained peak value becomes equal to the reference paper absent peak value Va0 under the environment at the time of the grammage detection. As described in the first exemplary embodiment, the ultrasonic wave is generated since the piezoelectric element of the transmission unit 31 oscillates by the input pulse voltage, and the amplitude level of the ultrasonic wave is thus proportional to the input pulse voltage. Therefore, when the input pulse voltage adjusted so as to establish Va=Va0 is set as Vi1, the ratio of Vi0 and Vi1 is equal to the ratio of Va1 and Va0 in Expression (2). Therefore, the following expression is obtained from Expression (2).

$$Vi0/Vi1=Va1/Va0=\alpha \quad \text{Expression (10)}$$

The measurement of the paper present peak value Vp is performed by the adjusted input pulse voltage Vi1, and the calculation coefficient $\tau$ is calculated by Expression (1). Then, from Expression (3) and Expression (10), the calculation coefficient it after the environment correction can be obtained by the following expression.

$$\tau r=\tau/(Vi0/Vi1) \quad \text{Expression (11)}$$

As described above, according to the present exemplary embodiment, the pulse voltage input to the transmission unit 31 is adjusted such that the value Va of the paper absent peak value obtained under the environment at the time of the grammage detection becomes equal to the reference paper absent peak value Va0. Accordingly, even when the surrounding environment is changed, it is possible to accurately detect the grammage of the recording material. In addition, it is possible to set the image forming conditions such as the optimal transfer condition and fixing condition for the second and subsequent recording materials.

Fourth Exemplary Embodiment

According to the first exemplary embodiment and the second exemplary embodiment, the ratio of the paper absent peak values in the reference environment and the environment when the grammage detection is performed is set as the environment correction coefficient $\alpha$, and the change in the surrounding environment is detected to perform the correction. However, in a case where the images are continuously formed on the plural sheets of the recording materials, the barometric pressure in the surrounding of the sensor is not likely to change in mid-course. Therefore, according to the present exemplary embodiment, a configuration for detecting and correcting a change in the temperature in the surrounding of the sensor will be described. Descriptions on main parts are similar to the first exemplary embodiment, and only parts different from the first exemplary embodiment will be described here.

As illustrated in FIG. 5A, when the surrounding temperature is changed from a relationship of Expression (12), the acoustic velocity v is changed, so that a time period until when the peak value is detected is changed.

$$v=331.5+0.607k \text{ [m/s] (}k\text{: Celsius temperature [°C.])} \quad \text{Expression (12)}$$

When a distance between the transmission unit 31 and the reception unit 32 is set as d, a counter frequency of the timer 345 is set as f, and a count value of the timer 345 at the time of the peak detection is set as t, the speed of the ultrasonic wave at the time of the measurement (acoustic velocity) v is obtained from Expression (13).

$$v=d/(t/f) \quad \text{Expression (13)}$$

According to the present exemplary embodiment, d=9 [mm] and f=3 [MHz] are set.

An acoustic velocity in an environment when the grammage detection is executed at the time of the start of the image formation to obtain the paper absent data Va1 is set as v1, and a surrounding temperature is set as Tk1. When an acoustic velocity in an environment when the grammage detection is executed during the paper absent period to obtain the paper absent data Van is set as vn, and a surrounding temperature is set as Tkn, a relationship as represented by Expression (14) is established. For that reason, the change in the surrounding temperature Tkn−Tk1 can be obtained from Expression (15).

$$vn-v1=(331.5+0.607\times Tkn)-(331.5+0.607\times Tk1)=0.607\times(Tkn-Tk1) \quad \text{Expression (14)}$$

$$(Tkn-Tk1)=(vn-v1)/0.607 \quad \text{Expression (15)}$$

On the other hand, an amount of change in the calculation coefficient $\tau$ accompanied by the change in the temperature can be obtained by way of experiment. For example, in FIG. 5B, the calculation coefficient of the paper having the grammage of 100 [g/m$^2$] indicates 0.0345 in the environment having the surrounding temperature at 20° C. and 0.0325 in the environment having the surrounding temperature at 40° C., so that the calculation coefficient is changed by 0.002. Therefore, a rate of change of the calculation coefficient $\tau$ by the surrounding temperature is (−0.002/0.0345)/(40° C.−20° C.)×100%=−0.3% when the environment at 20° C. is set as the reference. For that reason, when the surrounding temperature is increased by 1° C., the calculation coefficient $\tau$ is changed by −0.3%. In view of the above, the correction with respect to the change in the surrounding temperature can be executed by measuring the acoustic velocity in the environment when the paper absent data is obtained.

Figure 9A:
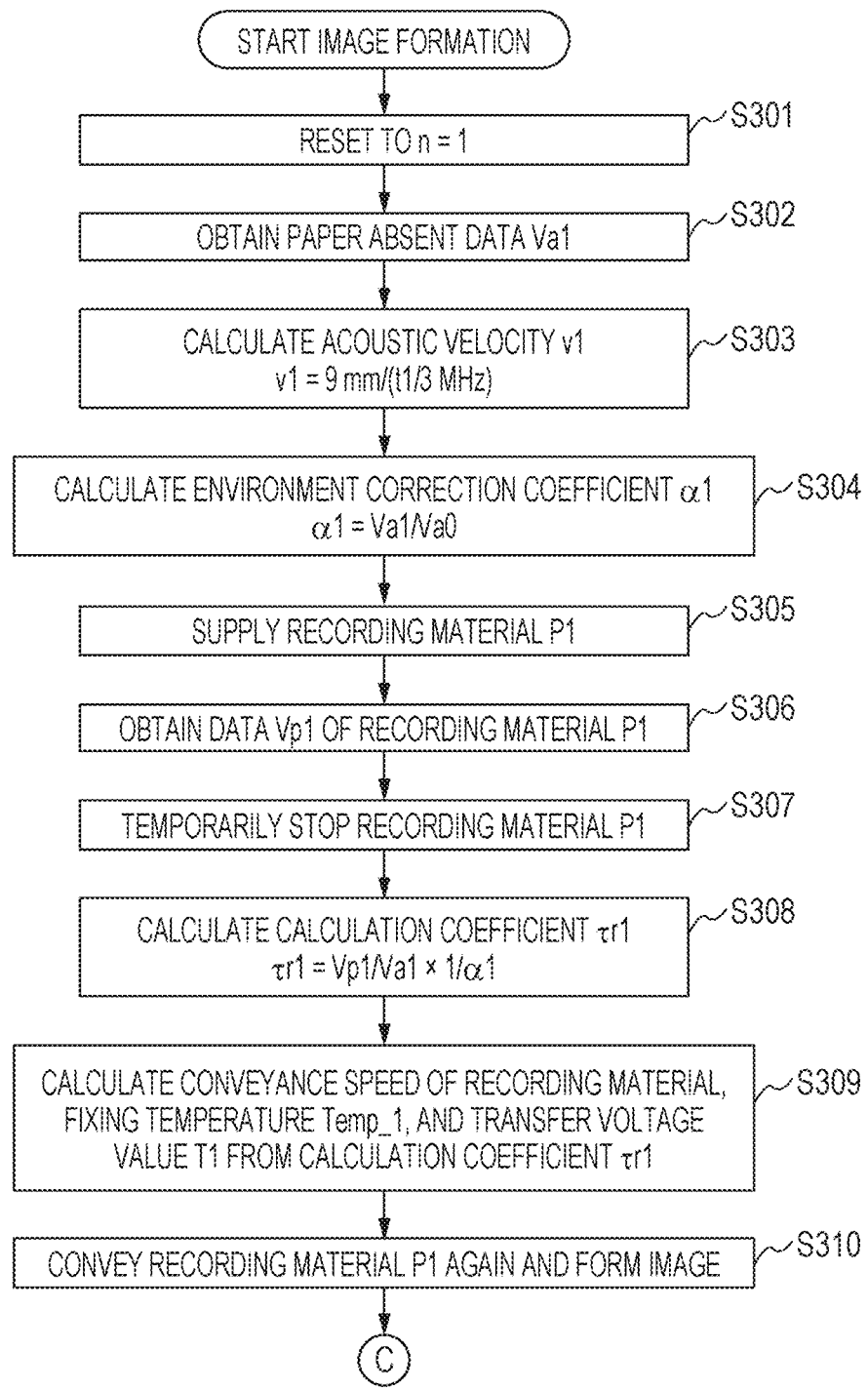
FIGS. 9A and 9B are flow charts during the image-forming period according to a fourth exemplary embodiment of the present invention.
Figure 9B:
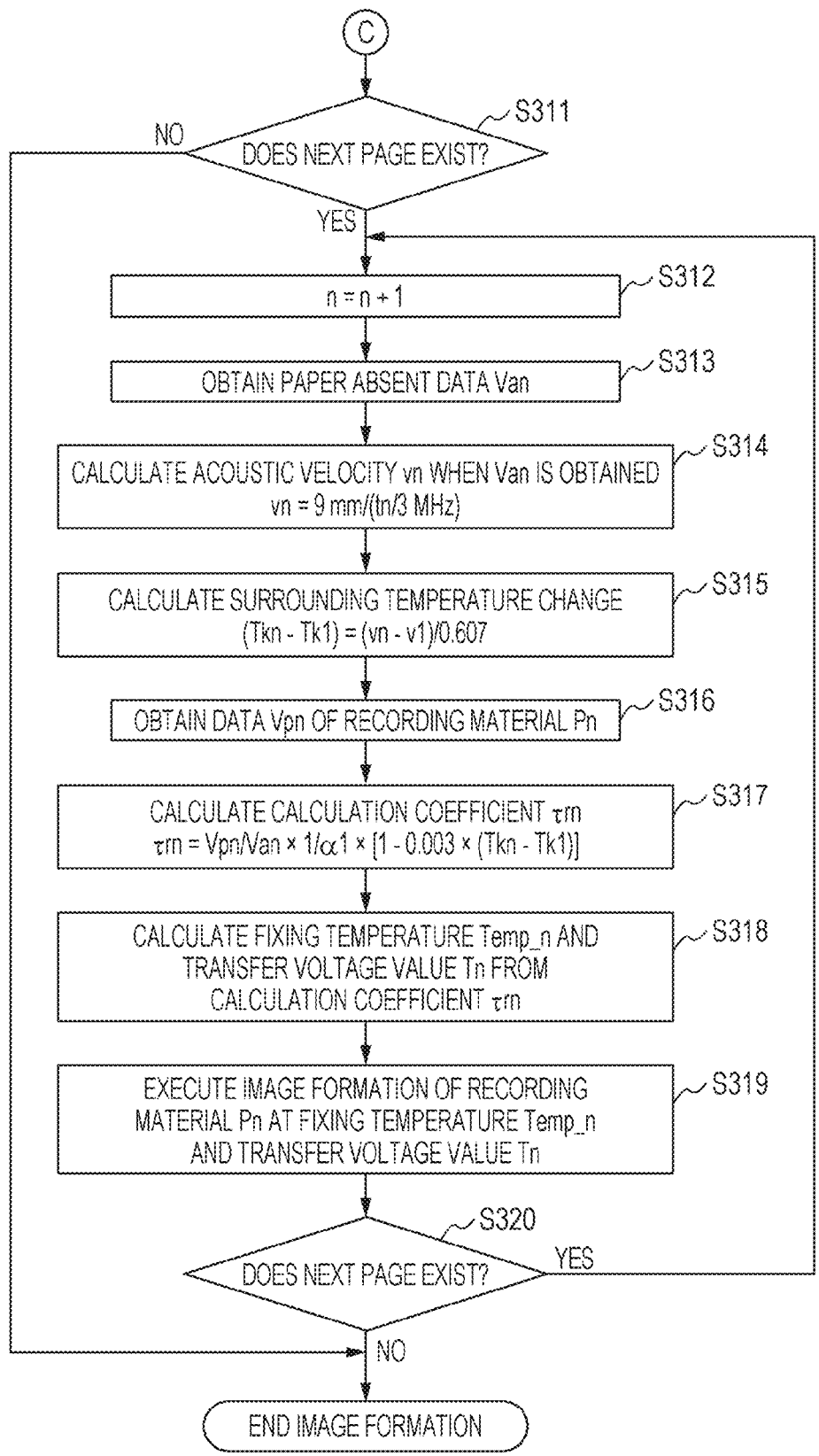

The image forming operation according to the present exemplary embodiment will be described by using flow charts of FIGS. 9A and 9B. A control based on the flow charts of FIGS. 9A and 9B is executed by the CPU 80 or the like on the basis of the program stored in the ROM (not illustrated).

The CPU 80 first resets the sheet number n to 1 after the image formation is started (S301). Subsequently, the grammage detection sensor 90 obtains the peak value by the above-described peak detection operation in the state where the paper is absent. At this time, the count values at the time of the detection of the respective peak values are also obtained. According to the present exemplary embodiment, the peak detection operation is performed 20 times at 10 ms intervals, and an average value of the peak values is set as the paper absent data Va1. Then, an average value of the count values is set as ta1 (S302). The acoustic velocity v1 is calculated from the count value ta1 by using Expression (13) (S303). Next, the environment correction coefficient α1 is calculated by dividing the paper absent data Va1 by the reference data Va0 at the time of the factory shipment which is stored in the storage unit 346 (S304). Subsequently, the CPU 80 supplies the recording material P1 from the supply cassette 2 (S305) and obtains the paper present data by performing the peak detection operation at a predetermined timing after the recording material P1 has reached the grammage detection sensor 90. In more detail, the peak detection operation is performed during a period from when the leading edge of the recording material P1 passes through the detection position 200 between the transmission unit 31 and the reception unit 32 until when the trailing edge of the recording material P1 reaches the detection position 200. According to the present exemplary embodiment, the peak detection operation is similarly performed 20 times at 10 ms intervals as in S302, and the average value of the peak values is set as the paper present data Vp1 (S306). Thereafter, the CPU 80 temporarily stops the recording material P1 (S307). Subsequently, the calculation coefficient τr1 normalized at 20° C. and 1 [atm] is calculated by using Expression (16) (S308), and the conveyance speed of the recording material, the fixing temperature Temp_1, and the transfer voltage value T1 are calculated from the calculated calculation coefficient τr1 (S309).

$$\tau r1 = Vp1/Va1 \times 1/\alpha 1 \quad \text{Expression (16)}$$

After the conditions are changed to the calculated conveyance speed of the recording material, the fixing temperature, and the transfer voltage value, the CPU 80 conveys the recording material P1 again to perform the image formation (S310). The CPU 80 checks the presence or absence of the following recording material in parallel with the image forming operation in S310 (S311). In a case where the following recording material is absent, the image formation is ended for no further operation. On the other hand, in a case where the following recording material is present, the sheet number n is incremented (S312), and the peak detection operation is performed during the paper absent period. In more detail, the peak detection operation is performed during the period from when the trailing edge of the recording material Pn−1 passes through the detection position 200 between the transmission unit 31 and the reception unit 32 until when the leading edge of the recording material Pn reaches the detection position 200. According to the present exemplary embodiment, the peak detection operation is performed 10 times at 10 ms intervals to calculate the average value of the peak values, so that the paper absent data Van is obtained during the paper absent period. At this time, the average value of the count values tan is also obtained from the count values at the time of the detection of the respective peak values (S313). In addition, the acoustic velocity vn is calculated from the count value tan by using Expression (13) (S314), and the change in the surrounding temperature is calculated by using Expression (15) (S315).

Subsequently, the peak detection operation is performed at a predetermined timing after the recording material Pn reaches the grammage detection sensor 90 to obtain the paper present data. In more detail, the peak detection operation is performed during the period from when the leading edge of the recording material Pn passes the detection position 200 between the transmission unit 31 and the reception unit 32 until when the trailing edge of the recording material Pn reaches the detection position 200. According to the present exemplary embodiment, the peak detection operation is similarly performed 20 times at 10 ms intervals as in S306, and the average value of the peak values is set as the paper present data Vpn (S316). Subsequently, the calculation coefficient τrn normalized at 20° C. and 1 [atm] is calculated by using Expression (17) (S317), and the fixing temperature Temp_n and the transfer voltage value Tn are calculated from the calculated calculation coefficient τrn (S318).

$$\tau rn = Vpn/Van \times 1/\alpha 1 \times [1 - 0.003 \times (Tkn - Tk1)] \quad \text{Expression (17)}$$

After the trailing edge of the recording material Pn−1 passes through the fixing unit 21, the CPU 80 changes the fixing temperature to Temp_n and changes the transfer voltage value to Tn to perform the image formation (S319). In parallel with the image forming operation in S320, the CPU 80 checks the presence or absence of the following recording material (S320). In a case where the following recording material is absent, the image formation is ended for no further operation. On the other hand, in a case where the following recording material is present, the flow returns to S312, and the image formation is continued until when the following recording material becomes absent.

In a case where the images are continuously formed on the plural sheets of the recording materials by performing the above-described operation, even when the surrounding temperature is changed, it is possible to accurately detect the grammage of the recording material. In addition, it is possible to set the image forming conditions such as the optimal transfer condition and fixing condition for the second and subsequent recording materials.

According to the above-described exemplary embodiment, the control of detecting the grammage of the recording material Pn by using the data detected during the paper absent period between the trailing edge of the recording material Pn−1 and the leading edge of the recording material Pn has been described. However, the configuration is not limited to the above. For example, the grammage of the recording material Pn+1 supplied after the recording material Pn may be detected by using the data detected during the paper absent period between the trailing edge of the recording material Pn−1 and the leading edge of the recording material Pn. That is, feedback to the detection result of any of the recording materials following the recording material Pn may be performed. Alternatively, the grammage of the recording material Pn−1 may be detected by using the data detected during the paper absent period between the trailing edge of the recording material Pn−1 and the leading edge of the recording material Pn. That is, feedback to the detection result of any of the recording materials preceding the recording material Pn may be performed. This control is effective in a configuration, for example, where a time period from when the grammage of the recording material Pn is detected by the grammage detection sensor 90 until when the image is formed on the recording material Pn is long. In a case where the images are continuously formed on the plural sheets of the recording materials by performing the above-described operation, even when the surrounding environment is changed, it is possible to accurately detect the grammage of the recording material. In addition, it is possible to set the image forming conditions such as the optimal transfer condition and fixing condition for the second and subsequent recording materials.

In addition, according to the above-described exemplary embodiment, a sensor configured to detect the leading edge and the trailing edge of the recording material P may be arranged on the upstream side in the conveyance direction of the recording material P with respect to the grammage detection sensor 90. This sensor includes, for example, the registration sensor 40 arranged on the upstream side with respect to the grammage detection sensor 90 and on the downstream side with respect to the nip portion (not illustrated) formed by the conveying roller 5 and the opposing roller 6 for the conveyance. The registration sensor 40 can detect the paper absent period by measuring a time period from when the trailing edge of the previously conveyed first recording material is detected until when the leading edge of the subsequently conveyed second recording material is detected by the timer included in the image formation control unit 3. Then, the number of times when the peak detection operation is performed may be changed on the basis of the detected paper absent period. That is, in a case where the paper absent period is long, the number of times when the peak detection operation is performed may be increased, and in a case where the paper absent period is short, the number of times when the peak detection operation is performed may be decreased. In addition, the registration sensor 40 also operates as a timing determination unit configured to determine a timing when transmission and reception operation of the ultrasonic wave by the grammage detection sensor 90 is performed.

When the first recording material is supplied from the supply cassette 2 by the supply roller 4, the following second recording material may be brought out together. In this case, the paper absent period between the first recording material and the second recording material is shorter than usual. Then, in a case where the paper absent period is shorter than a predetermined threshold, the peak detection operation cannot be performed even once in some cases. In the above-described case, the grammage of the recording material to be conveyed next may be detected by using the previous paper absent data. For example, in a case where the peak detection operation cannot be performed since the paper absent period between the second sheet and the third sheet is shorter than the predetermined threshold, the grammage of the third sheet is detected by using the paper absent data obtained during the paper absent period between the first sheet and the second sheet. This processing is not limited to the case where the peak detection operation cannot be performed even once. The processing may be applied to a case where the peak detection operation cannot be performed the number of times for calculating the accurate paper absent data (for example, 10 times).

In addition, according to the above-described exemplary embodiment, a case where the images are continuously formed on the plural sheets of the recording materials refers to the following state. For example, this refers to a case where during a period from when the image is formed on the first recording material until when the image is formed on the second recording material, an ending operation (post-rotation operation) of the member related to the image formation such as the fixing unit 21 is not performed.

In addition, according to the above-described exemplary embodiment, the configuration in which the recording material P1 corresponding to the first sheet is temporarily stopped has been described. However, the image formation may be performed without stopping the recording material P1.

In addition, according to the above-described exemplary embodiment, the configuration in which the grammage detection sensor 90 is provided while being fixed to the image forming apparatus 1 has been adopted, but the grammage detection sensor 90 may be configured to be detachably attached to the image forming apparatus 1. When the grammage detection sensor 90 is configured to be detachably attached, for example, the user may easily replace the grammage detection sensor 90 in a case where the grammage detection sensor 90 malfunctions.

In addition, according to the above-described exemplary embodiment, the grammage detection sensor 90 and the control unit such as the sensor control unit 30 or the CPU 80 may be integrated with each other and configured to be detachably attached to the image forming apparatus 1. In this manner, if the grammage detection sensor 90 and the control unit can be integrated with each other to be replaceable, in a case where a function of the grammage detection sensor 90 is updated or added, the user can easily replace the sensor with a sensor having the new function.

Furthermore, according to the above-described exemplary embodiment, the example of the laser beam printer has been illustrated, but the image forming apparatus to which the present invention is applied is not limited to this. A printer of another printing system such as an ink jet printer or a copier may also be used.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-262773, filed Dec. 19, 2013, and Japanese Patent Application No. 2014-238974, filed Nov. 26, 2014 which are hereby incorporated by reference herein in their entirety.

What is claimed is:

1. An ultrasonic wave sensor used in an image forming apparatus having an image forming unit for forming an image on a recording material and a control unit for controlling an image forming condition of the image forming unit when an image is formed on the recording material, comprising:
   a transmission unit configured to transmit an ultrasonic wave; and
   a reception unit configured to receive the ultrasonic wave transmitted from the transmission unit,
   wherein the ultrasonic wave sensor outputs a first ultrasonic wave and a second ultrasonic wave to the control unit so that the control unit controls the image forming condition, the first ultrasonic wave being received by the reception unit not via the recording material after the ultrasonic wave is transmitted by the transmission unit, and the second ultrasonic wave being received by the reception unit via the recording material after the ultrasonic wave is transmitted by the transmission unit,
   wherein a plurality of recording materials including a first recording material and a second recording material following the first recording material are continuously conveyed between the transmission unit and the reception unit,
   wherein in a case where an interval between a trailing edge of the first recording material and a leading edge of the second recording material is longer than a predetermined threshold, the ultrasonic wave sensor outputs the first ultrasonic wave and the second ultrasonic wave to the control unit so that the control unit controls the image forming condition when an image is formed on the second recording material, the first ultrasonic wave being received by the reception unit between the first recording material and the second recording material, and the second ultrasonic wave being received by the reception unit via the second recording material, and
   in a case where the interval is shorter than the predetermined threshold, the ultrasonic wave sensor outputs the first ultrasonic wave and the second ultrasonic wave to the control unit so that the control unit controls the image forming condition when the image is formed on the second recording material, the first ultrasonic wave being received by the reception unit before the first recording material reaches between the transmission unit and the reception unit, and the second ultrasonic wave being received by the reception unit via the second recording material.

2. The ultrasonic wave sensor according to claim 1, wherein the ultrasonic wave sensor and the control unit previously obtain the first ultrasonic wave received by the reception unit in a first environment, and wherein the ultrasonic wave sensor outputs to the control unit so that the control unit controls the image forming condition when the image is formed on the recording material in a second environment that is different from the first environment, the first ultrasonic wave received by the reception unit in the first environment, the first ultrasonic wave received by the reception unit in the second environment, and the second ultrasonic wave received by the reception unit in the second environment.

3. The ultrasonic wave sensor according to claim 2, wherein the ultrasonic wave sensor outputs to the control unit so that the control unit controls the image forming condition when the image is formed on the recording material in the second environment, an amplitude value of the first ultrasonic wave in the first environment, an amplitude value of the first ultrasonic wave in the second environment, and an amplitude value of the second ultrasonic wave in the second environment.

4. The ultrasonic wave sensor according to claim 2, wherein the transmission unit transmits the ultrasonic wave in accordance with an input drive signal, and wherein the ultrasonic wave sensor outputs to the control unit so that the control unit controls the image forming condition when the image is formed on the recording material in the second environment, a first drive signal causing an amplitude value of the first ultrasonic wave in the first environment to become a predetermined value, a second drive signal causing an amplitude value of the first ultrasonic wave in the second environment to become the predetermined value, and an amplitude value of the second ultrasonic wave in the second environment.

5. The ultrasonic wave sensor according to claim 2, wherein the ultrasonic wave sensor outputs to the control unit so that the control unit controls the image forming condition when the image is formed on the recording material in the second environment, a first period that is from when the transmission unit transmits an ultrasonic wave until when the reception unit receives the first ultrasonic wave in the first environment, a second period that is from when the transmission unit transmits an ultrasonic wave until when the reception unit receives the first ultrasonic wave in the second environment, and an amplitude value of the second ultrasonic wave in the second environment.

6. The ultrasonic wave sensor according to claim 2, wherein the environment is a barometric pressure or a temperature in a surrounding of the ultrasonic sensor.

7. An image forming apparatus comprising:
a transmission unit configured to transmit an ultrasonic wave;
a reception unit configured to receive the ultrasonic wave transmitted from the transmission unit;
a conveyance unit configured to convey a recording material between the transmission unit and the reception unit;
an image forming unit configured to form an image on the recording material conveyed by the conveyance unit; and
a control unit configured to control an image forming condition of the image forming unit when an image is formed on the recording material based on a first ultrasonic wave received by the reception unit not via the recording material after the ultrasonic wave is transmitted by the transmission unit, and a second ultrasonic wave received by the reception unit via the recording material after the ultrasonic wave is transmitted by the transmission unit, wherein the conveyance unit conveys a plurality of recording materials including a first recording material and a second recording material following the first recording material between the transmission unit and the reception unit, wherein in a case where an interval between a trailing edge of the first recording material and a leading edge of the second recording material is longer than a predetermined threshold, the control unit controls the image forming condition when an image is formed on the second recording material based on the first ultrasonic wave received by the reception unit between the first recording material and the second recording material, and the second ultrasonic wave received by the reception unit via the second recording material, and in a case where the interval is shorter than the predetermined threshold, the control unit controls the image forming condition when an image is formed on the second recording material based on the first ultrasonic wave received by the reception unit before the first recording material reaches between the transmission unit and the reception unit, and the second ultrasonic wave received by the reception unit via the second recording material.

8. The image forming apparatus according to claim 7, wherein the control unit does not stop an operation of the image forming unit during a period from when the image is formed by the image forming unit on the first recording material until when the image is formed on the second recording material.

9. The image forming apparatus according to claim 7, wherein the image forming condition is a temperature when the image is fixed on the recording material by a fixing unit included in the image forming unit, a voltage value supplied to a transfer unit included in the image forming unit, or a conveyance speed of the recording material.

10. The image forming apparatus according to claim 7, wherein the control unit previously obtains the first ultrasonic wave received by the reception unit in a first environment, wherein the control unit controls the image forming condition when the image is formed on the recording material in a second environment that is different from the first environment based on the first ultrasonic wave received by the reception unit in the first environment, the first ultrasonic wave received by the reception unit in the second environment, and the second ultrasonic wave received by the reception.

11. The image forming apparatus according to claim 10, wherein the control unit corrects an amplitude value of the second ultrasonic wave in the second environment based on an amplitude value of the first ultrasonic wave in the first environment and an amplitude value of the first ultrasonic wave in the second environment, and controls the image forming condition when the image is formed on the recording material in the second environment based on the corrected amplitude value of the second ultrasonic wave.

12. The image forming apparatus according to claim 10, wherein the transmission unit transmits the ultrasonic wave in accordance with an input drive signal, and wherein the control unit corrects the amplitude value of the second ultrasonic wave in the second environment based on a first drive signal at which the amplitude value of the first ultrasonic wave in the first environment becomes a predetermined value and a second drive signal at which the amplitude value of the first ultrasonic wave in the second environment becomes the predetermined value, and controls the image forming condition when the image is formed on the recording material in the second environment based on the corrected amplitude value of the second ultrasonic wave.

13. The image forming apparatus according to claim 10, wherein the control unit corrects the amplitude value of the second ultrasonic wave in the second environment based on a first time period from when the transmission unit transmits the ultrasonic wave until when the reception unit receives the first ultrasonic wave in the first environment and a second time period from when the transmission unit transmits the ultrasonic wave until when the reception unit receives the first ultrasonic wave in the second environment, and controls the image forming condition when the image is formed on the recording material in the second environment based on the corrected amplitude value of the second ultrasonic wave.

14. The image forming apparatus according to claim 10, wherein the environment is a barometric pressure or a temperature in a surrounding of the transmission unit or the reception unit.

15. The image forming apparatus according to claim 7, wherein, in a case where a interval is shorter than the predetermined threshold, the control unit controls the image forming condition when the image is formed on the second recording material based on the first ultrasonic wave received by the reception unit between a third recording material preceding the first recording material and the first recording material, and the second ultrasonic wave received by the reception unit via the second recording material.

16. The image forming apparatus according to claim 7, wherein, in a case where a interval is shorter than the predetermined threshold, the transmission unit doesn't transmit ultrasonic waves between the first recording material and the second recording material.

17. The image forming apparatus according to claim 7, wherein in the case where the interval is longer than the predetermined threshold, the reception unit is able to receive the first ultrasonic wave at least once between the first recording material and the second recording material, and in the case where the interval is shorter than the predetermined threshold, the reception unit is unable to receive the first ultrasonic wave between the first recording material and the second recording material.

18. The image forming apparatus according to claim 7, further comprising:
a detection unit configured to detect a leading edge and a trailing edge of a recording material conveyed by the conveyance unit,
wherein the control unit calculates the interval based on a time period from when the detection unit detects a trailing edge of the first recording material until when the detection unit detects a leading edge of the second recording material, and a conveyance speed of a recording material.

19. An image forming apparatus comprising:
a transmission unit configured to transmit an ultrasonic wave;
a reception unit configured to receive the ultrasonic wave transmitted from the transmission unit;
a conveyance unit configured to convey a recording material between the transmission unit and the reception unit;
an image forming unit configured to form an image on the recording material conveyed by the conveyance unit; and
a control unit configured to control an image forming condition of the image forming unit when an image is formed on the recording material based on a first ultrasonic wave received by the reception unit not via the recording material after the ultrasonic wave is transmitted by the transmission unit, and a second ultrasonic wave received by the reception unit via the recording material after the ultrasonic wave is transmitted by the transmission unit,
wherein the conveyance unit conveys a plurality of recording materials including a first recording material and a second recording material following the first recording material between the transmission unit and the reception unit,
wherein the control unit controls the image forming condition when an image is formed on the second recording material based on the first ultrasonic wave received by the reception unit before the first recording material reaches between the transmission unit and the reception unit, the first ultrasonic wave received by the reception unit between the first recording material and the second recording material, and the second ultrasonic wave received by the reception unit via the second recording material.

20. The image forming apparatus according to claim 19, wherein the control unit controls the image forming condition when the image is formed on the second recording material based on the first ultrasonic wave received by the reception unit between a third recording material preceding the first recording material and the first recording material, the first ultrasonic wave received by the reception unit between the first recording material and the second recording material, and the second ultrasonic wave received by the reception unit via the second recording material.

21. The image forming apparatus according to claim 20, wherein the control unit corrects an amplitude value of the second ultrasonic wave received by the reception unit via the second recording material based on an amplitude value of the first ultrasonic wave received by the reception unit between the third recording material and the first recording material, and an amplitude value of the first ultrasonic wave received by the reception unit between the first recording material and the second recording material, and
controls the image forming condition when the image is formed on the second recording material based on the corrected amplitude value of the second ultrasonic wave.

22. The image forming apparatus according to claim 19, wherein the control unit does not stop an operation of the image forming unit during a period from when the image is formed by the image forming unit on the first recording material until when the image is formed on the second recording material.

23. The image forming apparatus according to claim 19, wherein the image forming condition is a temperature when the image is fixed on the recording material by a fixing unit included in the image forming unit, a voltage value supplied to a transfer unit included in the image forming unit, or a conveyance speed of the recording material.

24. An ultrasonic wave sensor used in an image forming apparatus having an image forming unit for forming an image on a recording material and a control unit for controlling an image forming condition of the image forming unit when an image is formed on the recording material, comprising:
- a transmission unit configured to transmit an ultrasonic wave; and
- a reception unit configured to receive the ultrasonic wave transmitted from the transmission unit,
- wherein the ultrasonic wave sensor outputs a first ultrasonic wave and a second ultrasonic wave to the control unit so that the control unit controls the image forming condition, the first ultrasonic wave being received by the reception unit not via the recording material after the ultrasonic wave is transmitted by the transmission unit, and the second ultrasonic wave being received by the reception unit via the recording material after the ultrasonic wave is transmitted by the transmission unit,
- wherein a plurality of recording materials including a first recording material and a second recording material following the first recording material are conveyed between the transmission unit and the reception unit,
- wherein the ultrasonic wave sensor outputs to the control unit so that the control unit control the image forming condition when an image is formed on the second recording material, the first ultrasonic wave received by the reception unit before the first recording material reaches between the transmission unit and the reception unit, the first ultrasonic wave received by the reception unit between the first recording material and the second recording material, and the second ultrasonic wave received by the reception unit via the second recording material.

25. The ultrasonic wave sensor according to claim 24,
wherein the ultrasonic wave sensor outputs to the control unit so that the control unit controls the image forming condition when the image is formed on the second recording material, the first ultrasonic wave received by the reception unit between a third recording material preceding the first recording material and the first recording material, the first ultrasonic wave received by the reception unit between the first recording material and the second recording material, and the second ultrasonic wave received by the reception unit via the second recording material.

26. The ultrasonic wave sensor according to claim 25,
wherein the ultrasonic wave sensor outputs to the control unit so that the control unit controls the image forming condition when the image is formed on the second recording material, an amplitude value of the first ultrasonic wave received by the reception unit between the third recording material and the first recording material, and an amplitude value of the first ultrasonic wave received by the reception unit between the first recording material and the second recording material, and an amplitude value of the second ultrasonic wave received by the reception unit via the second recording material.

\* \* \* \* \*